(12) United States Patent
Movva

(10) Patent No.: US 10,902,090 B2
(45) Date of Patent: *Jan. 26, 2021

(54) METHODS AND SYSTEMS FOR REMOTELY DETERMINING LEVELS OF HEALTHCARE INTERVENTIONS

(71) Applicant: CarePredict, Inc., Plantation, FL (US)

(72) Inventor: Satish Movva, Davie, FL (US)

(73) Assignee: CarePredict, Inc., Plantation, FL (US)

( * ) Notice: Subject to any disclaimer, the term of this patent is extended or adjusted under 35 U.S.C. 154(b) by 410 days.

This patent is subject to a terminal disclaimer.

(21) Appl. No.: 15/703,507

(22) Filed: Sep. 13, 2017

(65) Prior Publication Data

US 2018/0025123 A1    Jan. 25, 2018

Related U.S. Application Data

(63) Continuation of application No. 13/896,306, filed on May 16, 2013, now Pat. No. 9,798,860.

(51) Int. Cl.
*G06Q 50/22* (2018.01)
*G06F 17/40* (2006.01)
(Continued)

(52) U.S. Cl.
CPC .......... *G06F 19/3418* (2013.01); *A61B 5/002* (2013.01); *A61B 5/0017* (2013.01); *A61B 5/0022* (2013.01); *A61B 5/1113* (2013.01); *A61B 5/1116* (2013.01); *A61B 5/1121* (2013.01); *A61B 5/1123* (2013.01);
(Continued)

(58) Field of Classification Search
CPC ........ G16H 50/20; G16H 10/60; G16H 50/30; G16H 40/67; G16H 50/70; G16H 40/63; G16H 40/20; G16H 70/60; G16H 20/30; G16H 10/65; G16H 20/10; G16H 50/50; G06Q 50/24; G06Q 10/0631; G06F 19/3456; G06F 19/3475; G06F 1/163; G06F 3/014; A61B 5/0024; A61B 5/0022;
(Continued)

(56) References Cited

U.S. PATENT DOCUMENTS

2006/0047538 A1   3/2006  Condurso et al.
2007/0294360 A1  12/2007  Ebling et al.
(Continued)

FOREIGN PATENT DOCUMENTS

KR   10-2009-0053250   5/2009
KR   10-2010-0042327   4/2010
(Continued)

OTHER PUBLICATIONS

Search Report from corresponding French Application No. 1757211, dated Jul. 10, 2018.
(Continued)

*Primary Examiner* — Maroun P Kanaan
(74) *Attorney, Agent, or Firm* — DLA Piper LLP (US)

(57) ABSTRACT

The present subject matter relates to methods and systems utilizing wearable sensor technology to determine when a patient's health may be degrading to trigger progressively higher levels of care and involvement, from "free" hands and eyes to skilled clinicians, in order to keep patients in the lowest cost setting of care, the home, for as long as possible.

30 Claims, 16 Drawing Sheets

Block diagram of Sensor

(51) Int. Cl.
- *G06Q 10/10* (2012.01)
- *G06F 19/00* (2018.01)
- *A61B 5/11* (2006.01)
- *A61B 5/00* (2006.01)
- *G16H 20/30* (2018.01)
- *G16H 50/70* (2018.01)
- *G16H 40/67* (2018.01)
- *A61B 5/053* (2006.01)
- *G16H 10/65* (2018.01)
- *G16H 40/63* (2018.01)

(52) U.S. Cl.
CPC .......... *A61B 5/1127* (2013.01); *A61B 5/7275* (2013.01); *A61B 5/747* (2013.01); *G06Q 50/22* (2013.01); *G16H 20/30* (2018.01); *G16H 40/67* (2018.01); *G16H 50/70* (2018.01); *A61B 5/0533* (2013.01); *A61B 5/1117* (2013.01); *A61B 5/1118* (2013.01); *A61B 5/6801* (2013.01); *A61B 5/6843* (2013.01); *A61B 2562/0219* (2013.01); *A61B 2562/0223* (2013.01); *A61B 2562/0271* (2013.01); *G16H 10/65* (2018.01); *G16H 40/63* (2018.01)

(58) Field of Classification Search
CPC ..... A61B 5/002; A61B 5/1117; A61B 5/6831; A61B 5/746; A61B 5/1113; A61B 5/1118
See application file for complete search history.

(56) References Cited

U.S. PATENT DOCUMENTS

| | | |
|---|---|---|
| 2008/0001735 A1 | 1/2008 | Tran |
| 2009/0278696 A1 | 11/2009 | Lindh et al. |
| 2012/0256742 A1 | 10/2012 | Snodgrass et al. |
| 2012/0259650 A1 | 10/2012 | Mallon et al. |
| 2013/0085780 A1 | 4/2013 | Braunstein et al. |
| 2013/0095459 A1* | 4/2013 | Tran ................ A61B 5/6816 434/247 |

FOREIGN PATENT DOCUMENTS

| | | |
|---|---|---|
| WO | 2003/044755 A1 | 5/2003 |
| WO | 2007/144419 | 12/2007 |

OTHER PUBLICATIONS

Notice of Preliminary Rejection, and its English translation, from corresponding Korean Divisional Patent Appln. No. 10-2018-0042187, dated Jul. 11, 2018.

Notice of Preliminary Rejection, and its English translation, from corresponding Korean Divisional Patent Appln. No. 10-2018-0107630, dated Jul. 29, 2019.

Search Report from corresponding French Application No. 2,838,232, dated Feb. 26, 2016.

Office Action from corresponding U.S. Appl. No. 14/674,813, dated Feb. 1, 2016.

Notice of Preliminary Rejection, and its English translation, from corresponding Korean Divisional Patent Appln. No. 10-2018-0107630, dated Nov. 12, 2018.

* cited by examiner

METHODS AND SYSTEMS FOR REMOTELY DETERMINING LEVELS OF HEALTHCARE INTERVENTIONS

TECHNICAL FIELD

The exemplary teachings herein pertain to methods and systems for determining levels of healthcare interventions, and in particular, to methods and systems which monitor a patients activity and location to determine if healthcare interventions are warranted, and what level of healthcare interventions are deemed necessary or required. Specifically, the present disclosure relates to methods and systems which keeps patients in the lowest cost setting of care, the home, for as long as possible, through the use of wearable sensor technology to determine when a patient's health may be degrading to trigger progressively higher levels of care and involvement, from "free" hands and eyes to skilled clinicians.

BACKGROUND

The Baby Boomer wave is yet to peak and already they are electing Medicare at the rate of 11,000 a day since June, 2012. Patients with chronic care conditions are on the rise, especially those with the so-called "life style" diseases such as Diabetes and Obesity. The funding model of our healthcare system cannot keep pace with the demand. As in any system, higher level of resources cost more. The highest cost care setting is the Hospital, and the lowest is care at home. Further, the staffing model of our healthcare system cannot keep pace with the demand. The ratio between available professional caregivers and seniors with healthcare needs is set to dramatically escalate as the baby boomer wave rolls inexorably towards its peak in 2023. The advantages of a low cost care setting can be wiped out in an instant, if the patient health degrades unnoticed and they end up in the ER or an Acute care setting.

The Patient Protection and Affordable Care Act (ACA) enshrines and encourages the concept of Accountable Care Organizations (ACO). According to the ACA, an ACC) "must define processes to promote evidence-based medicine and patient engagement, report on quality and cost measures, and coordinate care, such as through the use of tele-health, remote patient monitoring, and other such enabling technologies." In essence this means that healthcare providers are responsible for the outcomes of a patient even when the patient is not in their setting of care. For instance an ACO is still accountable when a patient is discharged to an Assisted Living Facility (ALF) or to home care to make certain the patient outcome remains positive, i.e., the ACO's are responsible for the patient outcome even when they are at home or in an ALF setting. This is ensured by the use of financial incentives to the ACO that maintains good patient outcomes. The ACA caused a large number of ACO's to form quickly and they usually consist of a hospital, physicians and increasingly post acute healthcare providers such as Home care or ALP.

The second aspect of the Affordable Care Act is the incentive to set up Health exchanges in which insurance companies compete to provide healthcare policies. Since pre-existing conditions and cherry picking of the insured are not allowed, this will cause these insurance companies, typically operating as Managed Care Organizations (MCO) to offer attractive benefits to obtain customers but will also force them to use cost containment models to make the care delivery very efficient.

The third aspect of the ACA is that state Medicaid enrollments are set to increase dramatically. Even before ACA, states such as Texas, New Jersey and others were experimenting with outsourcing their entire Medicaid populations to Managed Care entities primarily with a cost containment by utilization management goal. Medicaid populations have a high incidence of lifestyle diseases as well and a tendency to utilize high cost healthcare such as the Emergency Room. This Medicaid expansion brings into the main stream more patients who are homebound and/or have one or more chronic diseases, who were previously completely outside the healthcare system (due to lack of insurance), and whose healthcare system contact was primarily the ER, and who now will fall under the MCO umbrella. This additional patient load can be a very high utilizer of costly services.

Further, hospitals that participate in Medicare are now responsible for the patient's outcome even after discharge; in essence, if the patient is re-hospitalized within 30 days following discharge, for the same diagnosis that they were originally in the hospital for, then the hospital has to absorb all the costs for the patient's subsequent admission. In addition there is potential for extending this warranty period from 30 days to 60 days and beyond. This financial penalty makes the hospital acutely concerned for the patients' welfare post discharge and incentivizes the Hospital to offer services outside their four walls, out of their own pocket, to is make sure the patient is not readmitted unnecessarily. These services today range from having a home care agency check on the patient periodically in the 30 days and/or to assign a tele-monitor to remotely collect clinical data on the patient to try to see if a hospitalization is needed.

The use of Tele-Monitoring has been well documented for several decades. Tele-monitoring as used today is primarily a device installed in the home with various sensors such as Blood Pressure cuffs, pulse-oximetry and weight scales that are designed to collect clinical "Vitals" of the patient. These devices require the patient to be an active participant in the process and diligently use the device at prescribed times to collect the data. The device then transmits the data to a central clearing house or to a Live Ops center for action.

Tele-monitoring has been used extensively in the past to monitor "Clinical Vitals" such as pulse, blood oxygen levels, ECG, EEG etc. Tele-monitoring is usually not a wearable device but a static device in a home with various attachments that a patient needs to actively use at prescribed times by applying its various measuring devices to their body (ECG leads, pulse oximetry sensor, BP cuffs etc.). Tete-monitoring usually sends data to a LiveOps center where a nurse monitors readings and calls a patient back for abnormal vitals results. There is no inclusion of "free" resources such as resident caregivers, family and friends, to help determine the patient state. There is no tracking of functional state or detecting anomalies in patterns of activity.

The adoption of Tele-monitoring has not taken off primarily due to the high cost of these proprietary devices and lack of reimbursement from the payers for installing them in a patient home. An additional hurdle has been the requirement for active participation by the patient in using the devices.

In the early 2000's with the widespread availability of REID, several large companies (Intel, GE among others) tried to deploy the model of a fully instrumented patient home with the use of ambient monitoring. This ranged from sensors in the carpet to measure weight, to pressure mats that detect steps, to cameras that detect presence of the patient and attempt to deduce the activity they were involved in.

This overly ambitious idea failed due to several reasons: one being the very high cost of retrofitting a home for ambient monitoring systems (sensor laden carpets, door mats, cameras, wiring, RFID tags on everyday objects and REID readers), and a second being patient disenchantment with the surveillance systems that reeked of "big brother" style lack of privacy.

Ambient monitoring came into vogue with the widespread use of RFID in 2000. Ambient monitoring uses cameras, pressure mats, carpet sensors and RFID tags on household items to try to detect activity that a patient is engaged in. It is very expensive to fit a home with ambient monitoring. Mostly targeted towards group Senior Living Facilities, it is highly intrusive and the lack of privacy means low adoption rates. Also, ambient monitoring has trouble distinguishing the patient from other residents. Wearable sensors bypass the need for ambient monitoring as the patient is instrumented and not the home.

Wearable Sensors utilizing MEMS (Micro Electro Mechanical Systems) are ubiquitous now in personal health and fitness (e.g., fitbit, Jawbone, Nike etc.). Sensors typically have Accelerometers, Gyros, Inclinometers and Magnetometers among other MEMS. Sensors can detect walking, running, sleeping, sitting, falling, and rolling among other functional states of a wearer by combining the readings from the multiple on-board MEMS. Sensors can have radios to communicate with a base station, smartphone, computing device or directly to the internet.

Over the last 3-5 years and especially the last 12 months, there has been a sharp increase in the number of health and fitness devices targeting consumers directly. These range from wearable sensors for counting steps, sleep state, and other fitness metrics to disease monitoring is by use of clinical FDA approved consumer devices such as blood pressure monitors, weight scales, BMI and heart monitors. One common aspect of these devices is that they all interact with a consumer's Tablet, Smartphone or other computing device and present information graphically to the consumer. Some also allow the data to be uploaded to a web site and either printed and shared with a clinician, or in a few cases to be sent to a Clinician's email, or in rare cases to be sent electronically to the system the Clinician uses to store that patient's records. In almost all cases, these readings sit unattended until the clinician and patient have another reason to interact, such as a scheduled appointment. This is because the U.S. health care system is still based on a patient encounter between a Clinician and Patient to trigger any kind of interaction with the patient measurements.

Unlike the methods and systems of the present disclosure, other than recent use in fall detection, wearable MEMS sensors have not been used previously in a home setting with patients. Sensors have not been used as near real-time feedback sources in remote monitoring of directed demonstration of activity that is disease specific. Wearable sensors have not been used previously in a home setting with patients to track activity and track which room/area of a home the activity occurs in to deduce type of activity.

Further, unlike the methods and systems of the present disclosure, systems have not previously been used in conjunction with remote sensors to predict disease progression or decline in functional status of a patient in a home setting. Systems have not been used previously to ask disease specific questions in an automated manner (previously this required a clinical actor to present questions, observe patient and record answers). Automated systems have not been used previously to ask resident care givers, family members and friends of a patient to actively participate in the observation and interrogation of a patient with disease specific questions. Also, automated systems have not been used to triage through all available "free" resources before progressively costly resources are utilized.

Accordingly, to address the above stated issues, a method and system for remotely determining the need for healthcare interventions, and which keeps patients in the lowest cost setting of care, the home, for as long as possible is needed. The methods and systems disclosed herein fulfill such needs, and the costs and disadvantages associated with prior attempts at tele-monitoring, ambient monitoring and/or consumer self-monitoring are diminished or eliminated. It is desired that the disclosed methods and systems for providing the above benefits be applicable to any instances or applications wherein a patient's health is monitored to determine healthcare interventions.

SUMMARY

The exemplary technique(s), system(s) and method(s) presented herein relate to methods and systems for remotely determining levels of healthcare interventions, comprising wearable sensor technology in association with a computerized system utilizing a set of software and databases operating on a set of physical hardware in a remote location. The system monitors a patients activity and location, and determines when a patient who may have one or more chronic diseases or is otherwise homebound, requires progressively higher levels of care from family member interventions to a nurse phone call, to a medication change, to a nurse visit, to a physician visits and to a hospital visit.

Most patients have varying circles of care surrounding them from a resident spouse or other family caregiver, to non-resident family members or friends to nurses from home care agencies to physicians and finally hospitals. However, the first two circles of care, resident family caregiver and family members/friends, are not actively involved in the chain of care is today. They are passive bystanders for the most part even though they are the most readily available, have a vested interest and are in effect "free" hands and eyes in the care of the patient. By using sensors to detect change in a patient's functional state or to detect changes in patterns of activities of daily living of the patient, the disclosed methods and systems co-opt the available family caregivers or family members to act as eyes and ears to observe and report the state of the patient and to interrogate and report answers from the patient based on clinically established and disease specific questions generated by the disclosed methods and systems, as well as general questions to establish that the state of the patient is congruent with the system determination. This is the lowest cost steady state both in funding and staffing for patients who are either elderly or have a history of hospitalization or have one or more chronic care conditions.

The data from the sensors in conjunction with data observed/reported by members of the immediate circles of care is used to determine the likelihood that a patient may need a higher cost clinical intervention such as a nurse phone call to the patient, a nurse visit to the patient, a physician appointment or communication to a physician to change meds, or ultimately hospitalization.

This conservative and progressive escalation to higher levels of care is attractive to both the ACO and MCO customers as they struggle to manage outcomes (and thus reimbursement) as well as manage scarce resources in human staff. Both ACOs and MCOs prefer a low cost steady state to a high cost asymptotic event such as a hospital admission being the first inkling that a member patient health had deteriorated. Further, this model wherein family resources are being activated by the System first promotes a caring social network around a patient that could foster a better quality of life. Previously, family members and friends were only aware post an adverse event and could not help prior to that, as they were more likely not aware of the gradual decline that the System is now able to detect and warn.

Accordingly, it is an object of the methods and systems disclosed herein to function as an early warning system to all persons involved with a patient, including the ACO/MCO, that a patient degradation is underway and to help trigger proportionately increasing levels of interventions to return the patient to positive outcomes.

It is another object of the methods and systems disclosed herein to utilize the lowest cost resources, for instance technology and "free" eyes and ears in terms of resident caregivers or non-resident family members and friends, in its capacity as a sentinel or early warning system that only progressively escalates to higher cost interventions.

It is another object of the methods and systems disclosed herein to utilize passive monitoring of functional state and detection of activity patterns and deviations as an indicator of health state, and to co-opt the caregivers around a patient into being the remote "eyes and ears" in collecting additional data and validating the determination for care.

It is another object of the methods and systems disclosed herein to utilize an unobtrusive sensor that is worn on the body and which integrates room/area identification, to allow the system to deduce activity the patient maybe involved in without encroaching on their privacy.

It is another object of the methods and systems disclosed herein to use the readings from the wearable sensor to drive immediate automated analysis and activate the different levels of care surrounding a patient to get additional information, to confirm predicted trends, and ultimately be an early warning system that raises an alert to a Clinician before the patient deteriorates too far to be managed cost effectively.

It is another object of the methods and systems disclosed herein to utilize a sentinel system in conjunction with patient education on wellness and management of their disease through healthier styles.

Additional objects, advantages and novel features will be set forth in part in the description which follows, and in part will become apparent to those skilled in the art upon examination of the following and the accompanying drawings or may be learned by production or operation of the examples.

BRIEF DESCRIPTION OF THE DRAWINGS

The drawing figures depict one or more implementations in accord with the present teachings, by way of example only, not by way of limitation. In the drawing figures, like reference numerals refer to the same or similar elements.

DETAILED DESCRIPTION

The following description refers to numerous specific details which are set forth by way of examples to provide a thorough understanding of the relevant methods) and system (s). It should be apparent to those skilled in the art that the present disclosure may be practiced without such details. In other instances, well known methods, procedures, components, and circuitry have been described at a relatively high-level, without detail, in order to avoid unnecessarily obscuring aspects of the present disclosure. While the description refers by way of example to methods and systems for determining healthcare interventions, it should be understood that the method(s) and system(s) described herein may be used in any situation where a patient's health is monitored.

As discussed in more detail below, the system comprises a wearable sensor, a plurality of infrared beacons, and a communication system in association with a computerized system utilizing a set of software and databases operating on a set of physical hardware in a remote location. The system utilizes passive monitoring of the functional state of a patient, and detection of activity patterns of a patient, and deviations thereof, to determine the health state of a patient. The system utilizes this health state determination to co-opt the various levels of caregivers around a patient to collect additional data and validate the determination for care.

The system is configured for the patient with a set of data. For example, including but not limited to, diseases present, patient address, contact info, availability and types of computing device for use by patient, availability and number of telephone for use by patient, family caregiver contact info and computing device info, family members contact info and computing device info, ACO affiliation, MCO affiliation Hospital affiliation, Physicians of record, Case manger of record, Geriatric counselor of record, Pharmacies and contact info, Insurance info, type of residence, number of rooms, type of each room, base station type, communication medium and its configuration, number of beacons, type of beacons.

The home the patient lives in maybe equipped with low power infrared beacons ("Beacon") which transmit a unique ID representing the area of a home they are affixed in. For example Stove/Kitchen, Toilet/Bathroom etc. These are self installed devices that are fixed at a range of prescribed heights and operate on self contained power or utility power.

Figure 1:
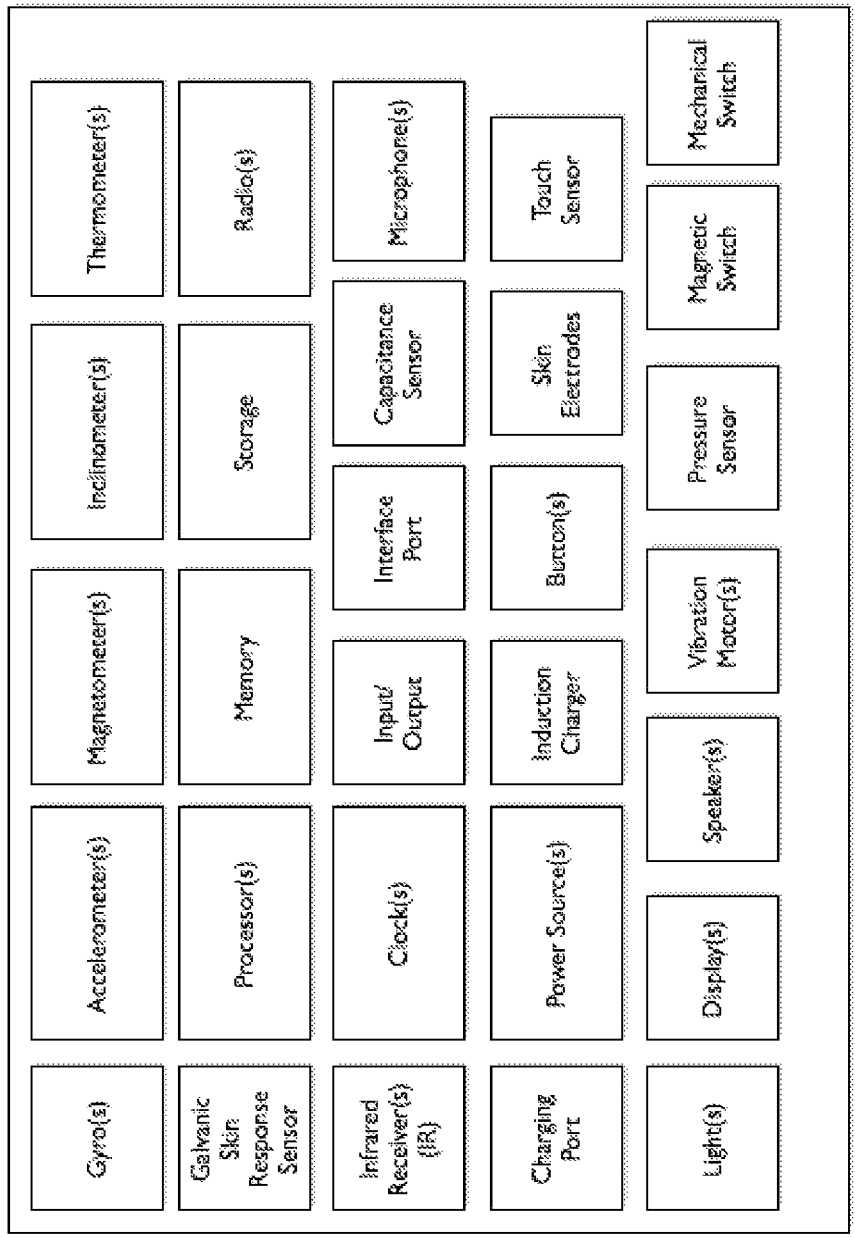
FIG. 1 is a block diagram of the components of the sensor of an exemplary embodiment of the system of the present disclosure.

The patient wears a wearable sensor apparatus, which is worn on the body. The placement of the Sensor may range from head, neck, chest, waist, upper hand, forearm, the wrist, hand, upper or lower thigh or lower extremities and the ideal placement may be recommended based on the disease state and physical ability and condition of the Patient. The Sensor may be worn under certain types of clothing as well that allows infrared beams to pass through. The Sensor may have one or more adjustable band, bracelet, strap, lanyards to allow it to be worn. The Sensor may be constructed to be liquid proof or liquid resistant FIG. 1 is a block diagram of the components of the sensor of an exemplary embodiment of the system of the present disclosure. As can be seen in FIG. 1, the Sensor contains various sensing devices such as, one or more Gyros, Accelerometers, Magnetometers, Inclinometers, Thermometers, and/or Galvanic Skin Response (GSR) sensors to detect the motion and state of the person and direction of travel/orientation of person wearing it. The Sensor also includes one or more Infrared receivers, or other suitable types of receivers, capable of sensing external infrared beams, or other suitable types of transmissions, and decoding the data embedded therein. The infrared receivers contained in the Sensor are capable of discriminating among multiple infrared beams and deducing the strength of the beam and thus the distance to the beam transmitter. One or more of the infrared receivers may be arranged on the Sensor to assist in beam triangulation to increase accuracy in determining direction, strength and distance to the beam transmitters.

Additionally, the Sensor contains a processing unit, memory and storage as required for a computing device. The Sensor runs operating system software and application software that allows the Sensor to be programmed to perform actions based on events. The Sensor may contain or more radios such as a WiFi radio, a Bluetooth radio, a cellular data modem radio, a Zigbee radio, a XBee radio. The Sensor may contain one or more interface ports for the Sensor to be programmed, tested, charged or for data to be communicated into or out of the Sensor. The Sensor contains one or more fixed or removable power sources to operate independently of external power. The Sensor may contain one or more charging ports to charge the internal power source. The Sensor may contain one or more induction charging circuits for the internal power source to be charged using a charging surface such as a charging mat, charging dongle, and/or charging cradle. The Sensor may contain one or more indicators to inform the user visually or aurally of the state of the charge within the internal power source.

The Sensor may also contain one or more output devices to convey information such as lights, vibration motors, display units, and/or speakers. The Sensor may contain one or more input devices to interact with the user such as microphones, buttons, and touch sensors. The Sensor may also employ its internal sensing devices to interact such as for example single tap on the device to display visually or aurally the battery level or double tap to cause it to synchronize data outside its normal schedule.

Still further, the Sensor may employ various sensing devices such as one or more capacitance sensors, skin electrodes, pressure sensors, magnetic switches and/or mechanical switches, to assist in detecting when it is being worn. The Sensor can record and report when it is not being worn and can report data related to how often it is being worn and how often it is not. The Sensor can make deductions on the activity and posture of the patient (e.g., sleeping, sitting, reclining, prone, supine, walking, running, shuffling, and/or falling). The Sensor can determine which local area (room) of a structure (home) or a specific area (Toilet) within a local area (Bathroom) of a structure (home) the patient is proximal to by means of an infrared receiver receiving the signals from the Beacon and deducing the location by the IDs of the one or more beacons visible to the infrared receiver(s).

The Sensor can determine which activity the patient is engaged in by the combination of the functional activity type (e.g., walking, sitting, reclining, standing, and/or lying down) and the area/room they are in when performing such activity. For instance, when the room detected is a bathroom and posture detected is sitting, this may indicate with a high likelihood that the person is using the toilet.

The Sensor may contain one or more internal clocks to provide time base and time reference. The Sensor aggregates data from its sensing devices and timestamps all data. The Sensor deduces activity of the patient based on the aggregation of the data from its sensing devices. The Sensor is capable of storing onboard, information deduced from the sensing devices readings and worn status.

The Sensor periodically checks to see if a connection is available to the internet either via a Base Station (if one is configured), or through a smart phone (if one is configured), a WiFi network (if one is configured), an onboard or outboard cellular data modem (if one is configured or is present onboard). If a base station is configured, the Sensor may communicate to it using a low power short range radio frequency protocol such as Bluetooth, Zigbee, XBee or WiFi. If a smartphone is configured, the Sensor may communicate to it using a low power short range radio frequency protocol such as Bluetooth, NFC, or WiFi. If an outboard cellular data modem is configured, the Sensor may communicate to it using a low power short range radio frequency protocol such as Bluetooth, NFC, or WiFi. If an onboard cellular data modem is configured, the Sensor may communicate to it using internal bus protocols such as i2c, NXP, Serial or other internal intra-component, intra circuit board or inter component and inter circuit board protocols. The Sensor periodically communicates via the Internet and uploads data into one or more databases and software systems ("System") at a remote location.

It is foreseen that the sensor and or system can be integrated with or to various other sensors such as Blood Pressure cuffs, pulse-oximetry, weight scales, sensors for counting steps, sleep state, and other fitness metrics, blood pressure monitors, BMI and/or heart rate monitors. The system can consume the readings from one or more of these devices to add data points to its prediction analysis.

Figure 2:
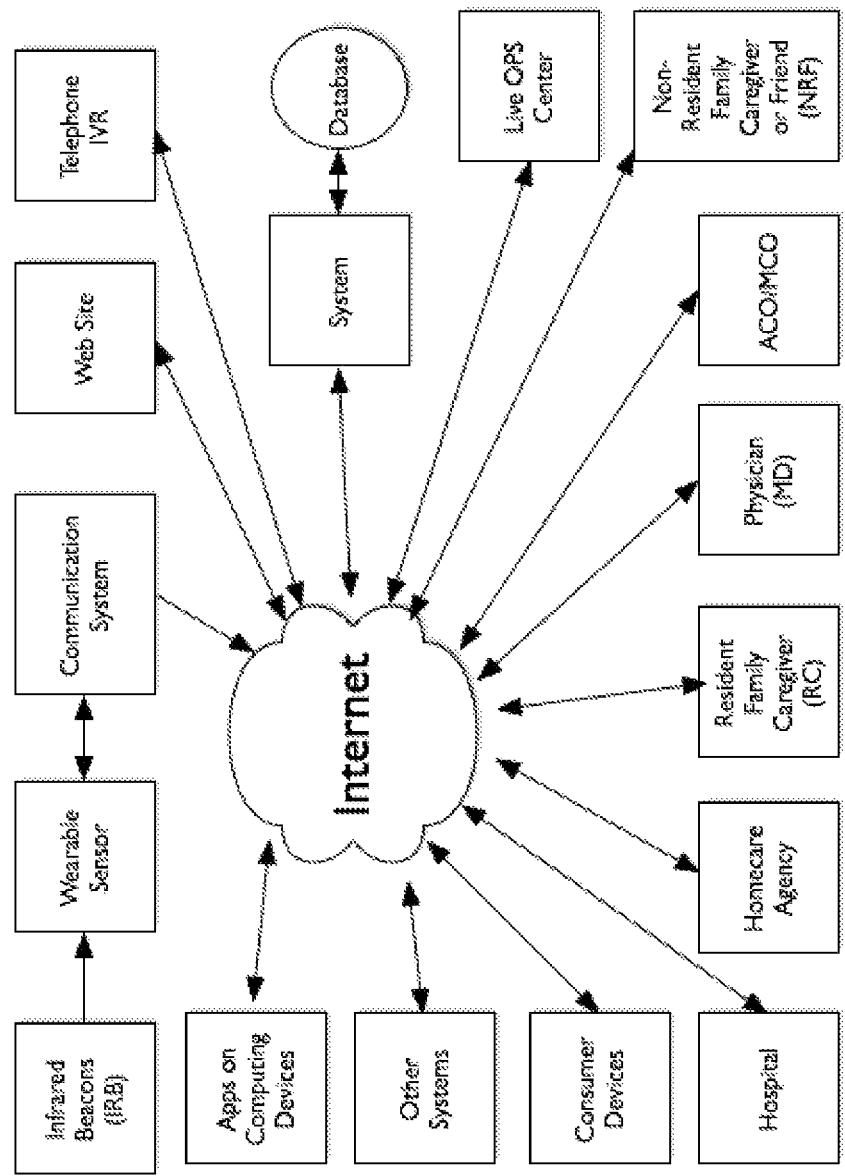
FIG. 2 is a block diagram of an exemplary embodiment of the system of the present disclosure.

FIG. 2 is a Hock diagram of an exemplary embodiment of the system of the present disclosure. The System is comprised of a set of software and databases operating on a set of physical hardware in a remote location. The System can send and receive data through the Internet to Sensors, Base Stations, other Devices such as but not limited to patient self-monitoring devices, other Systems, Computing devices, web sites, and Smartphones. The System can be accessed by various persons via the Internet using a web browser, and System presents information relevant to the person viewing it. The System can send and receive data to and from one or more Sensors worn by one or more Patients. The System can send and receive data to and from Software Applications running on computing devices such as but not limited to Smart Phones, Tablets and Computers. The System stores the received data into one or more databases. The System can communicate with multiple other Systems, Devices and Communications networks.

The System actively monitors usage data sent by the Sensor (being worn or not), and can initiate notifications in a progressively escalating manner if the device is not being used as intended. The System creates a baseline for activity using the first n days of received data, where n is configurable. The received data may originate from, but is not limited to, the Sensor, Other Systems, Consumer Devices, responses to questions on configured computing devices of resident family caregiver, non-resident family members, patient, Telephone IVR, clinicians, live ops center, physician, hospital and/or diagnostic labs.

The System analyzes the data and applies various algorithms based on but not limited to: a) one or more diseases of the person (e.g., CHF, Diabetes, Hypertension COPD, etc.); b) deduce functional level by how much activity the patient is engaged in; c) analyze for changes in activity pattern from previously learned patterns of activity; d) deduce from the data such as change in gait, number of steps taken, amount of activity, etc., if the person is degrading; e) deduce if the person has fallen by applying an algorithm to the sensor accelerometer data, room/area the person is in, position of the person now (e.g., supine, prone, reclining, etc.), and length of time with limited motion, repeated motions to achieve a standing position, crawling motions, and if body position is appropriate normally for the room/area person is now in.

The System sends a notification to the patient's configured computing device (Tablet/Phone/Computer) if one is configured. The notification will cause the application on the computing device to present specific questions. These questions will be based on the disease state of the patient and are well established in the academia as to their predictive value. The questions may have an interrogatory component where the app poses questions to the patient and accepts their responses. The system gathers the responses from the local application and adds them to its database(s). The software then analyses the additional data to see if escalation to next level, status quo, or de-escalation is appropriate. If the patient does not answer or respond to the application prompts, the System may escalate to the next level of care.

Based upon the sensed information, the System can additionally ask the patient to demonstrate a disease specific activity such as "walk twenty steps," and use the sensor to detect demonstration of the activity, time taken to complete activity, and/or vital signs before, during and after the activity, etc., and at its completion ask follow-up questions based upon the sensed information, such as "are you short of breath," etc. The system stores the responses for analysis and scoring according to established clinical guidelines. Thus, the system, based upon its analysis of sensed information, can automatically initiate patient tasks or tests, physical and/or mental, and evaluate patient performance of these tasks or tests in real-time.

If the patient is not capable of using a computing device, the System is configured to cause a telephone IVR system to call the patient. The Telephone IVR system will ask questions of the Patient such as for example "Press 1 if you are feeling pain", "Press 2 if you took your meds today", "Press 3 if you had a bowel movement", "Press 4 if you are feeling short of breath", and/or "Press 5 if your ankles are swollen". These questions will be based on the disease state of the patient and are well established in the academia as to their predictive value. The System gathers the responses from the IVR system and adds them to the database(s). The System then analyzes the additional data to see if escalation to next level, status quo, or de-escalation is appropriate.

The software, depending on the analysis of sensed information and/or responses to questions, sends a notification to the configured computing device of a resident caregiver who is in the same home as the Patient. (First level of the "Circles of Care"). The notification will cause the application on the computing device to present specific questions. These questions will be based on the disease state of the patient and are well established in the academia as to their predictive value. The questions will have an observational component where the resident caregiver answers questions on the observed state and behavior of the patient. The other questions will have an interrogatory component where the resident caregiver poses questions to the patient and enters their responses. The System gathers the responses and adds them to the database(s). The System then analyzes the additional data to see if escalation to next level, status quo, or de-escalation is appropriate.

The software, depending on the analysis of sensed information and/or responses to questions, sends a notification to the configured computing device of the next level of non-resident family members (siblings, sons/daughters, etc., who may not be residing in the same vicinity as patient) and/or friends. (Second level of the "Circles of Care"). The notification will cause the application on the computing device to present specific questions. These questions will be based on the disease state of the patient and are well established in the academia as to their predictive value. If the family member or friend is physically in the same vicinity as the patient (the application provides the choice on whether they are physically with the patient) then the questions will have an observational component where the family member or friend answers questions on the observed state and behavior of the patient. The other questions will have an interrogatory component where the family member or friend poses questions to the patient and enters their responses. The System gathers the responses and adds them to the database(s). The System then analyzes the additional data to see if escalation to next level, status quo, or de-escalation is appropriate.

If escalation is required based on all the data gathered thus far, the software sends a notification to the configured computing device(s) at a Live Ops center or other computing device where trained nurses or other clinical contacts review the data, call the Patient and/or resident family caregiver and/or other family members or friends. (Third level of the "Circles of Care"). The notification may cause the Nurse to call the patient with specific clinical questions based on their diseases, functional status, observed and reported state. The notification may cause the Nurse to call the resident caregiver with specific questions based on the patient diseases, functional status, observed and reported state. The notification may cause the Nurse to call the non-resident family member or friend with specific questions based on the patient diseases, functional status, observed and reported state. The system gathers the responses and adds them to the database. The Nurse is then offered a choice to escalate to next level, maintain status quo, or de-escalate to a lower level.

If escalation is chosen, the Nurse can escalate to the next necessary or desired step(s), which may be an in person visit, consult with physician to change medication, schedule a physician appointment for the patient, or arrange for hospitalization. (Fourth level of the "Circles of Care"). All stakeholders in the 1st-3rd levels of the "Circles of Care" are notified of escalation. If Status Quo is chosen, all stakeholders in the 1st-3rd levels of the "Circles of Care" are notified of status quo and optionally additional instructions on what changes in patient state to look for. A follow-up (notification) to 1st-3rd levels is scheduled by the system to ask follow-up questions identified by the nurse. If de-escalation is chosen, all stakeholders in the 1st-3rd levels of the "Circles of Care" are notified of de-escalation and optionally additional instructions on what changes in patient state to look for.

Figure 3:
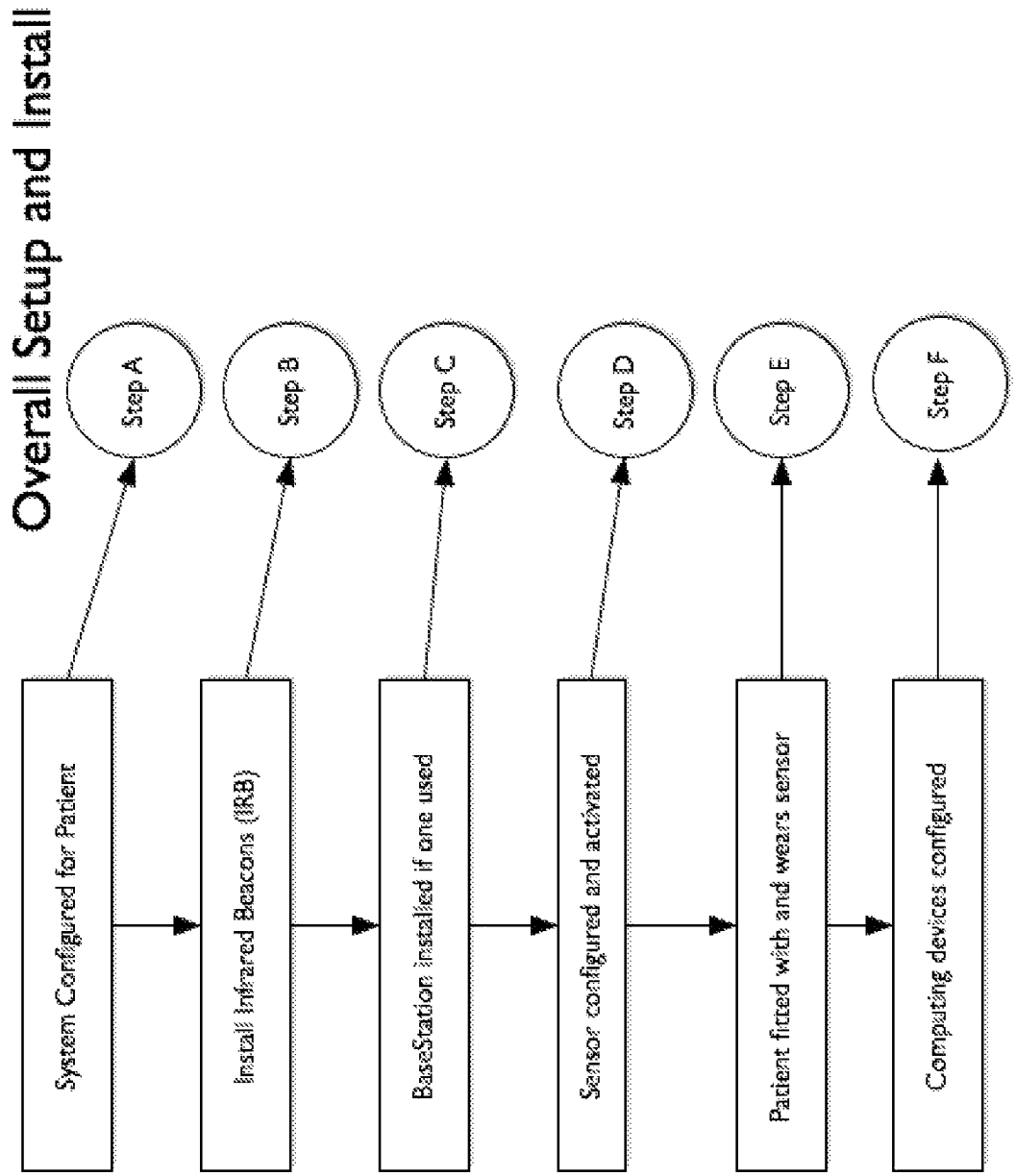
FIG. 3 is a flow chart of the overall setup and installation of an exemplary embodiment of the method and system of the present disclosure.
Figure 4A:
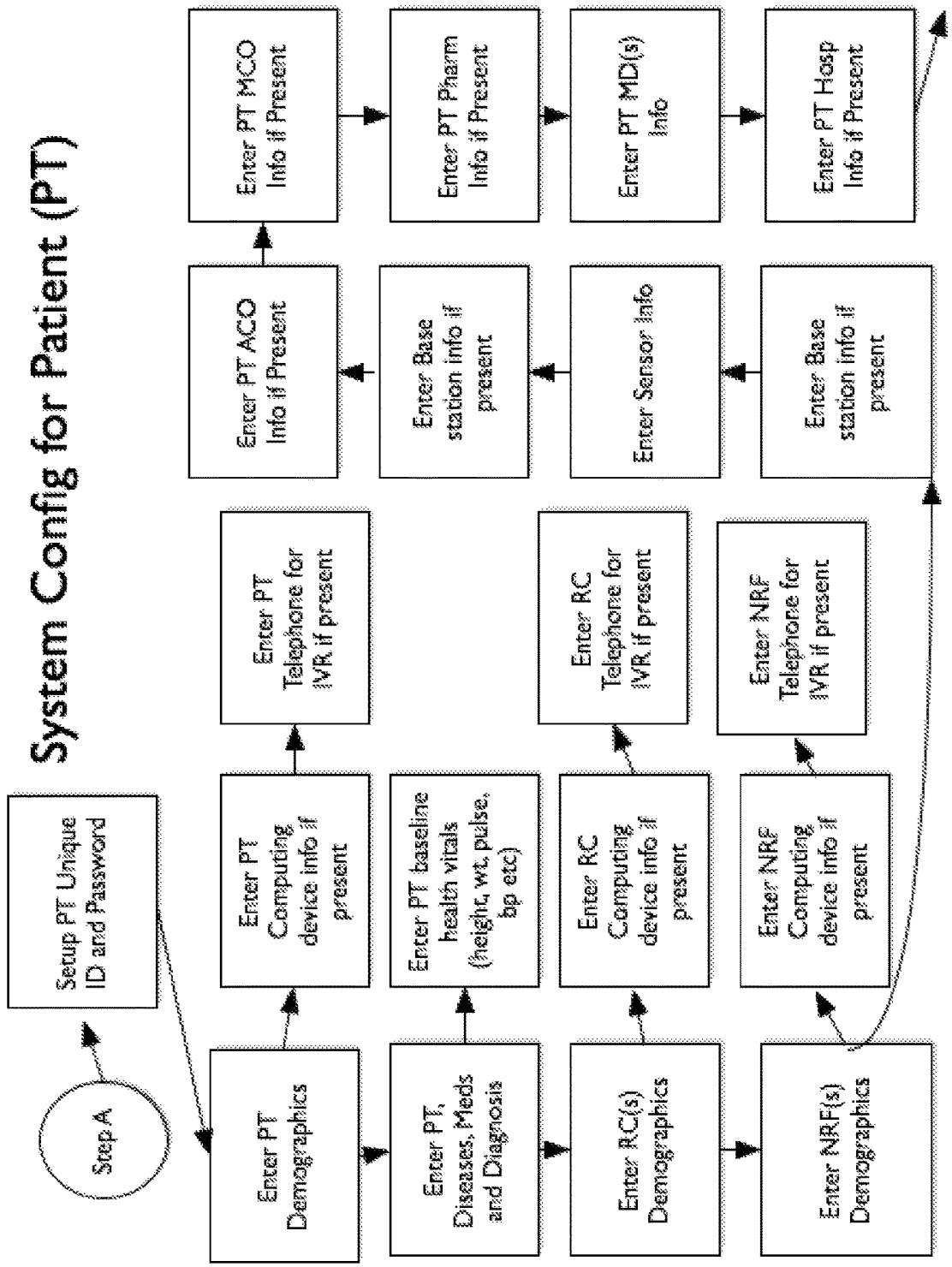
FIG. 4A is a flow chart for the system configuration for a patient of an exemplary embodiment of the method and system of the present disclosure.
Figure 4B:
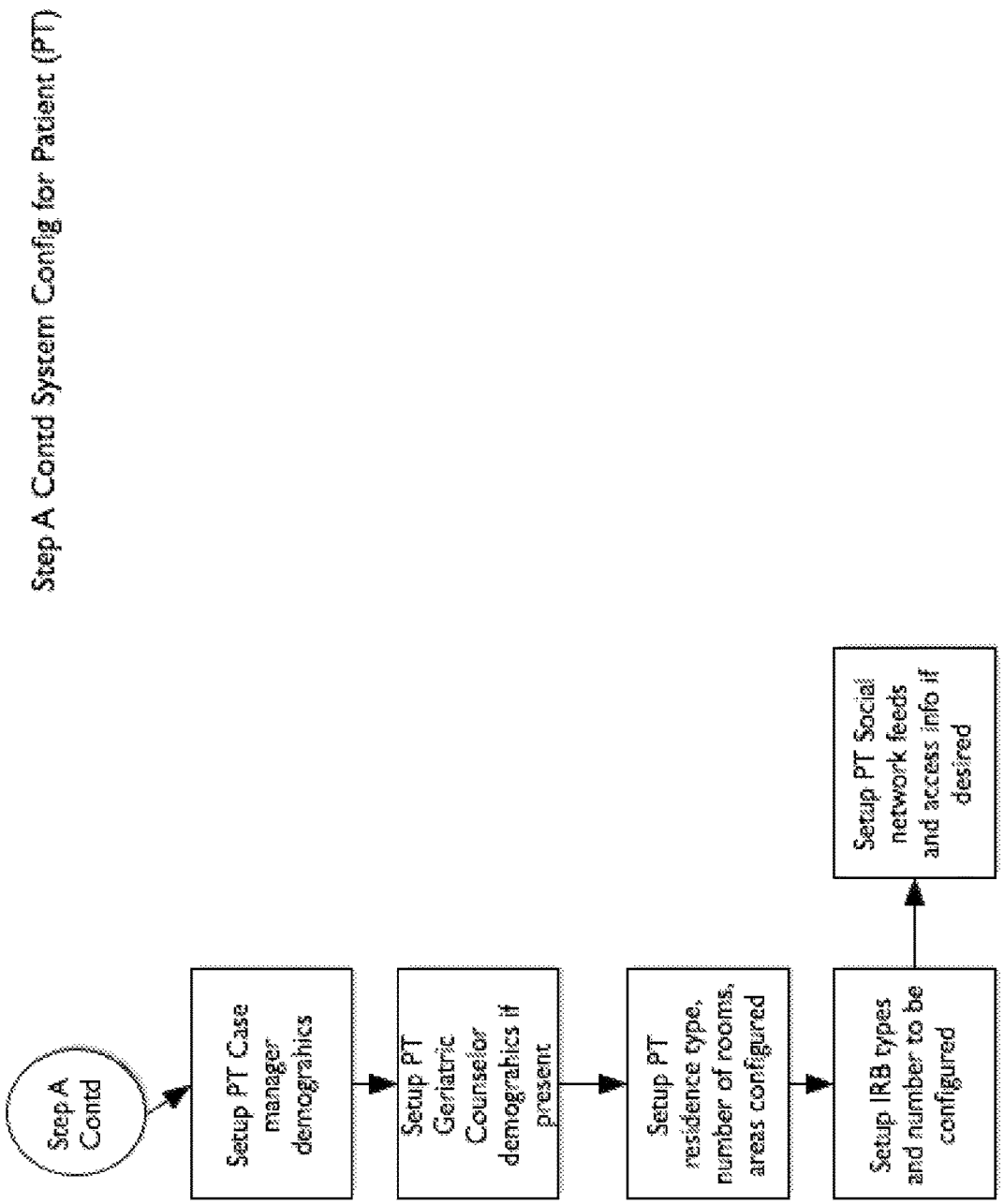
FIG. 4B is a flow chart for the system configuration for a patient, continued from FIG. 4A, of an exemplary embodiment of the method and system of the present disclosure.
Figure 5:
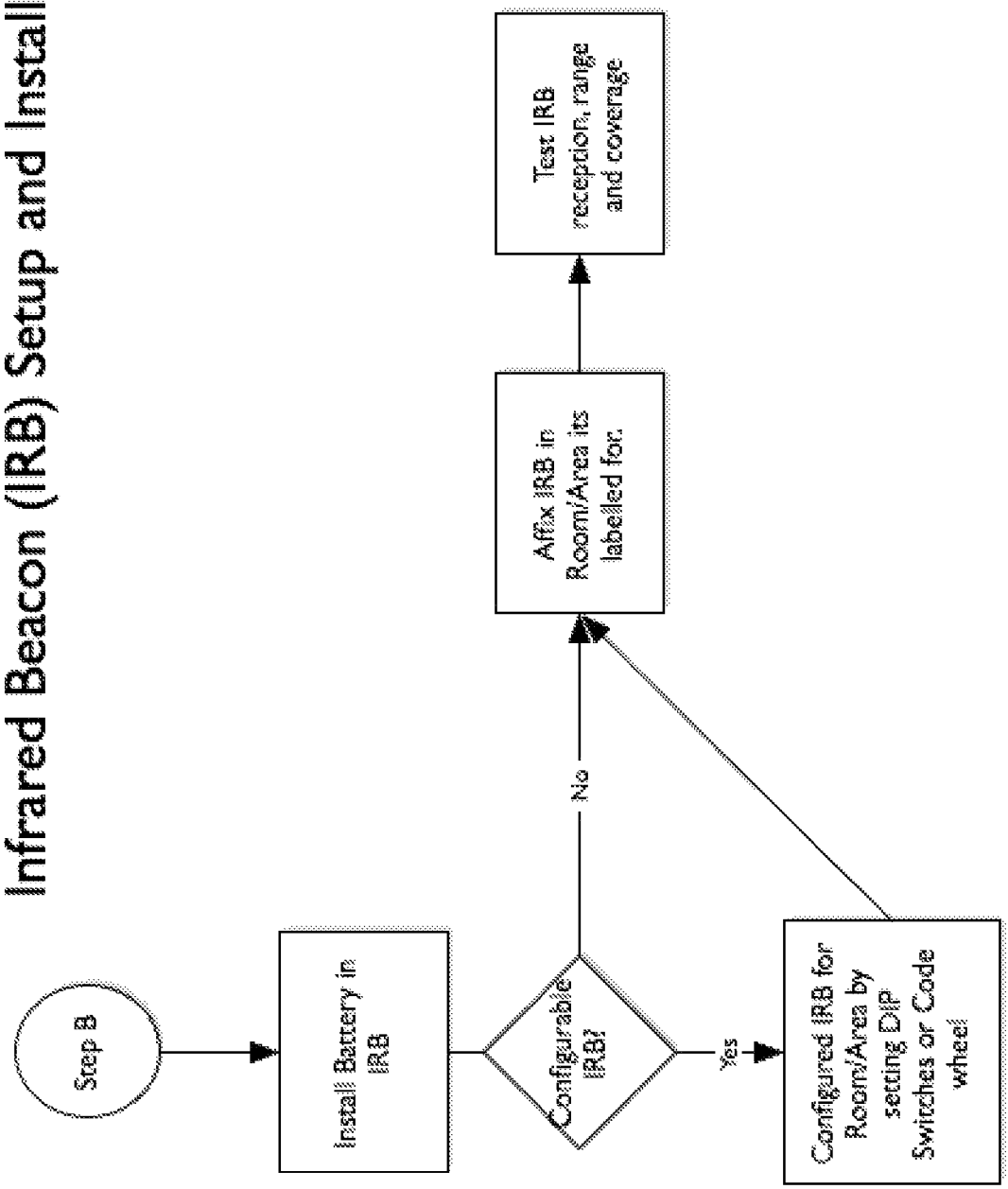
FIG. 5 is a flow chart for the infrared beacon setup and installation of an exemplary embodiment of the method and system of the present disclosure.
Figure 6:
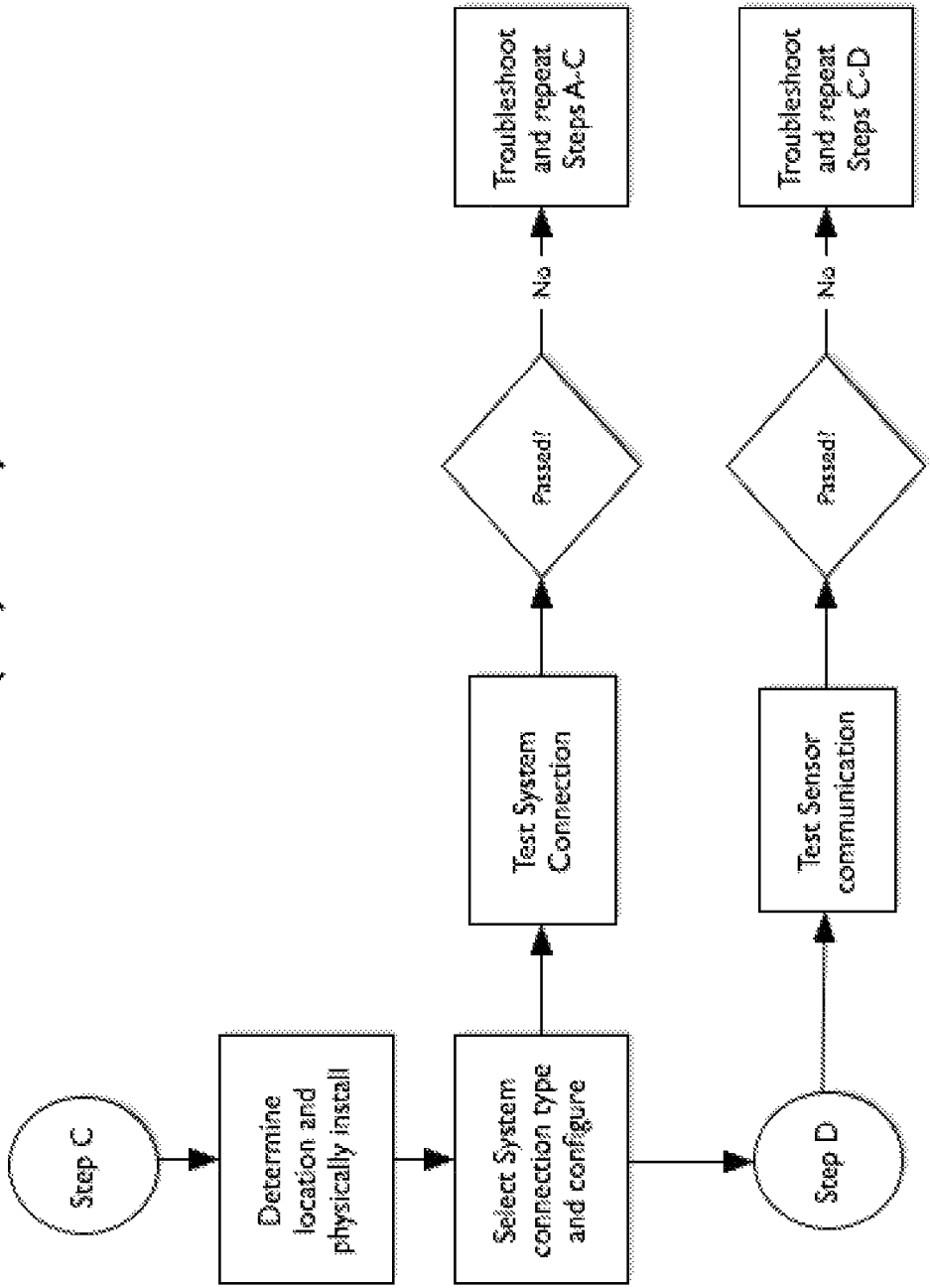
FIG. 6 is a flow chart for the base station setup and installation of an exemplary embodiment of the method and system of the present disclosure.
Figure 7:
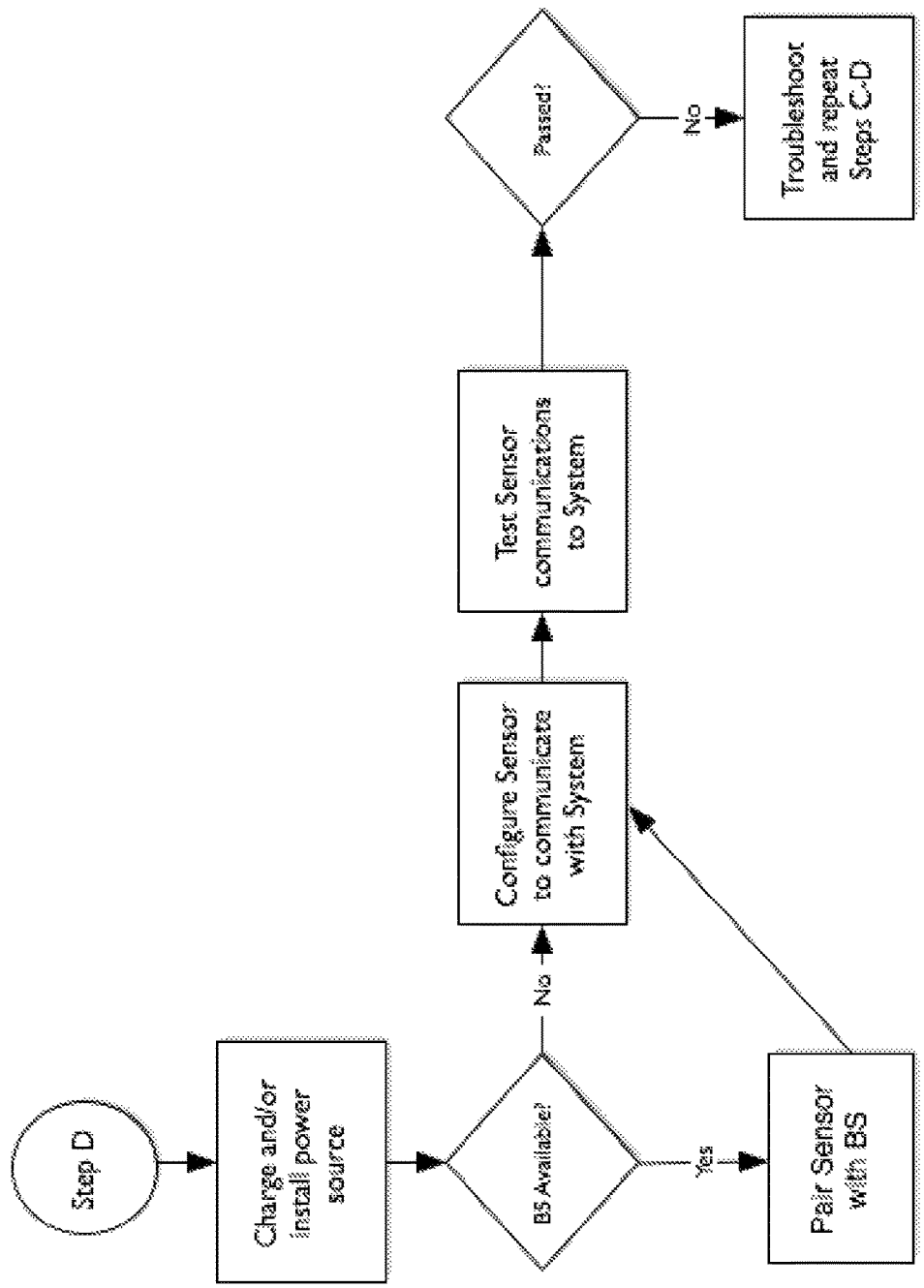
FIG. 7 is a flow chart for the sensor setup and installation of an exemplary embodiment of the method and system of the present disclosure.
Figure 8:
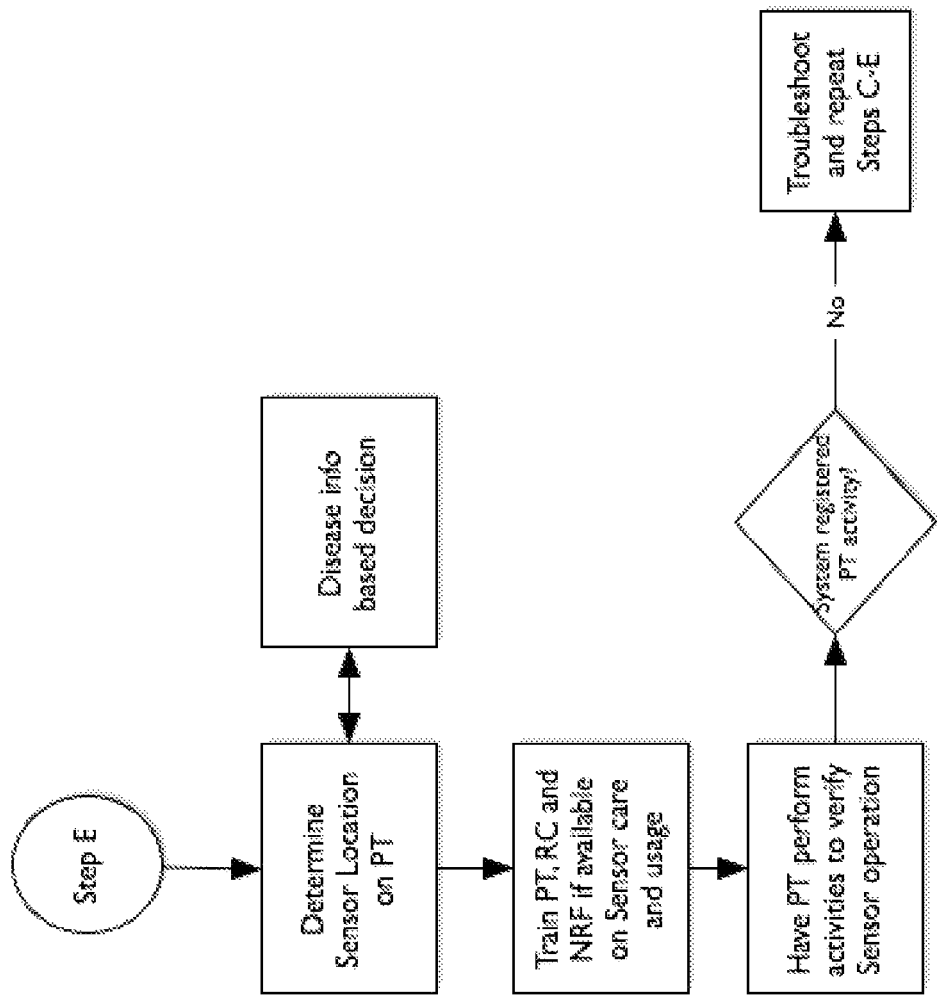
FIG. 8 is a flow chart for the sensor fitting on a patient of an exemplary embodiment of the method and system of the present disclosure.
Figure 9:
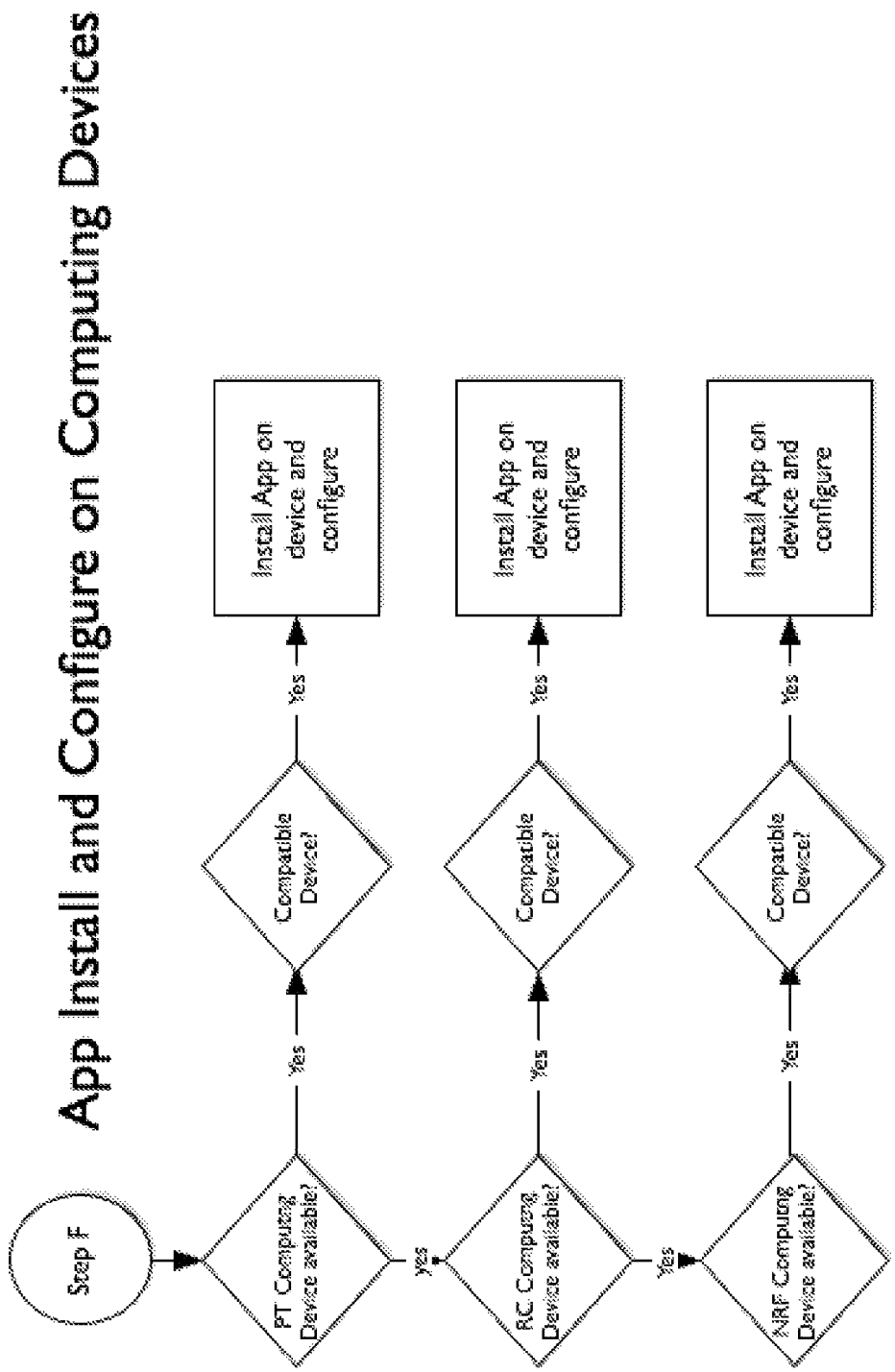
FIG. 9 is a flow chart for the software application installation and configuration on computing devices of an exemplary embodiment of the method and system of the present disclosure.

FIG. 3 is a flow chart of the overall setup and installation of an exemplary embodiment of the method and system of the present disclosure. As can be seen in FIG. 3, the overall system can be set up and installed in six steps, in the exemplary embodiment illustrated. In Step A, the system is configured for a patient, as illustrated in FIGS. 4A and 4B discussed below. In Step B, the Infrared Beacons are set up and installed, as illustrated in FIG. 5 discussed below. In Step C, the Base Station is set up and installed, as illustrated in FIG. 6 discussed below. In Step D, the Sensor is set up and installed, as illustrated in FIG. 7 discussed below. In Step E, the Sensor is fitted on the patient, as illustrated in FIG. 8 discussed below. In Step F, the application software (App) is installed and configured on computing devices used with the system, as illustrated in FIG. 9 discussed below.

Referring to FIGS. 4A and 4B, a flow chart for the system configuration for a patient is disclosed. The system configuration for a patient preferably comprises the following steps: setup a patient unique IL) and password; enter patient demographics, computing device information if present, and telephone for IVR if present; enter patient diseases, medications, and diagnosis, and patient baseline health vitals (height, weight, pulse, blood pressure etc.); enter Resident Caregiver(s) demographics, computing device info if present, and telephone for IVR if present; enter Non-resident Family member(s) and/or friends demographics, computing device info if present, and telephone for if present; enter Sensor information; enter Base station information if present; enter patient ACO information if present; enter patient MCO information if present; enter patient pharmacy information if present; enter patient doctor information; enter patient hospital information if present; setup patient case manager demographics; setup patient geriatric counselor demographics if present; setup patient residence type, number of rooms, areas configured; set up infrared beacon types and number to be configured; and setup patient social network feeds and access information if desired.

Referring to FIG. 5, a flow chart for the infrared beacon setup and installation is disclosed. The infrared beacon setup preferably comprises the following steps: install battery in the infrared beacon(s); if the beacon is configurable, then configure the beacon for room/area by setting DIP switches or code wheel; affix the beacon in the room/area it is labeled for; and test the beacon reception, range and coverage.

Referring to FIG. 6, a flow chart for the base station setup and installation is disclosed. The base station setup and installation preferably comprises the following steps: determine location and physically install; select system connection type and configure; test system connection; if the system connection did not pass the test, then troubleshoot and repeat. Steps A-C.

Referring to FIG. 7, a flow chart for the sensor setup and installation is disclosed. The sensor setup and installation preferably comprises the following steps: charge and/or install power source; if the base system is available, then pair the sensor with the base system; if the base system is not available, the configure the sensor to communicate with the system; test the sensor communications to the system; and if the sensor communications did not pass the test, then troubleshoot and repeat steps C-D.

Referring to FIG. 8, a flow chart for the sensor fitting on the patient is disclosed. The sensor fitting on the patient preferably comprises the following steps: determine sensor location on the patient based upon the disease information of the patient; train patient, resident caregiver and non-resident family member or friend, if available, on sensor care and usage; have patient perform activities to verify sensor operation; if the system does not properly register patient activity, then troubleshoot and repeat Steps C-E.

Referring to FIG. 9, a flow chart for the software application installation and configuration on computing devices is disclosed. The software application installation and configuration on computing devices preferably comprises the following steps: if a patient computing device is available, then determine if the device is compatible with the system, and if compatible, install the software application on the patient device and configure; if a resident caregiver computing device is available, then determine if the device is compatible with the system, and if compatible, install the software application on the resident caregiver device and configure; and if a non-resident family member or friend computing device is available, then determine if the device is compatible with the system, and if compatible, install the software application on the non-resident family member/ friend device and configure.

Figure 10:
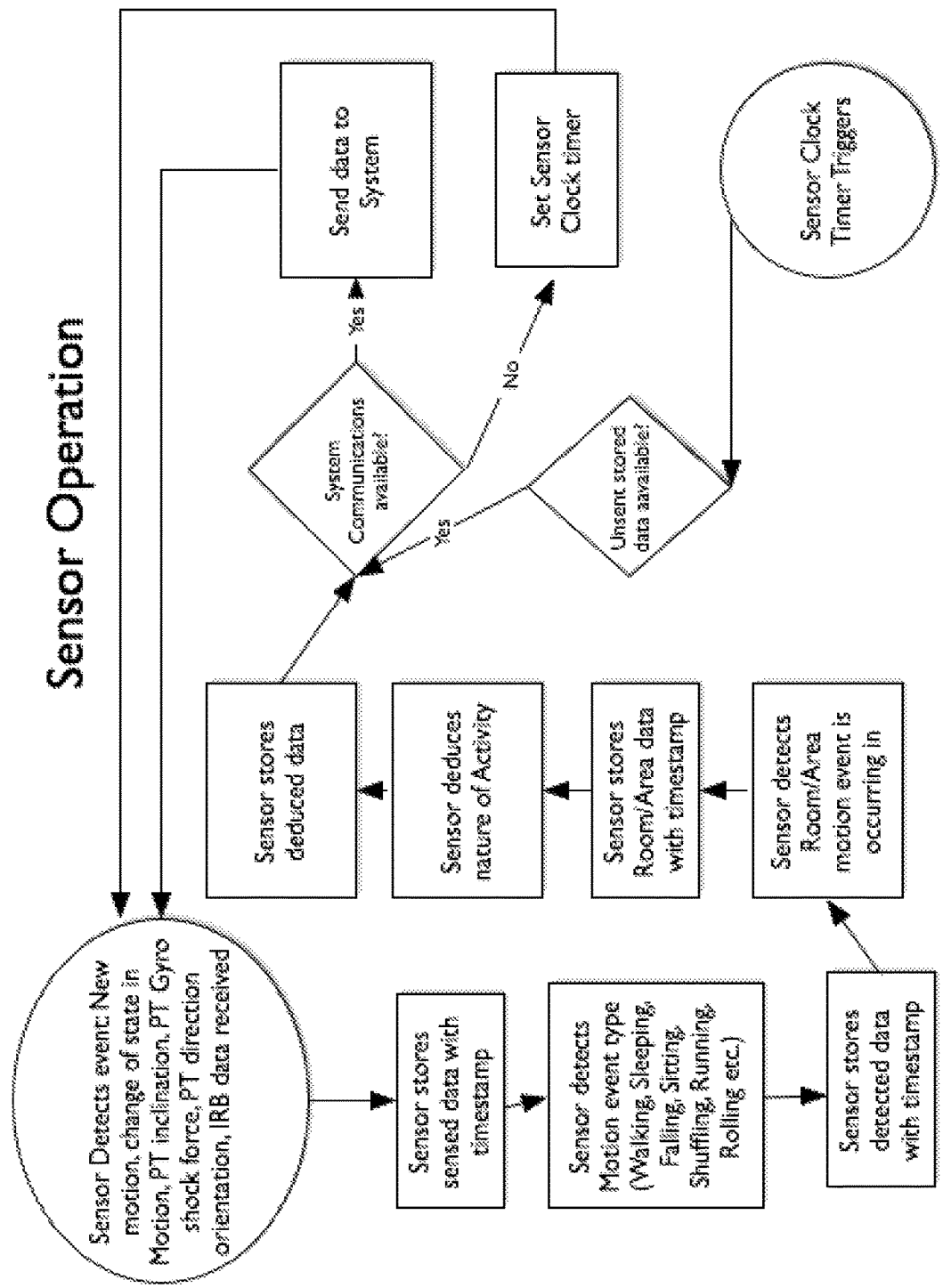
FIG. 10 is a flow chart for the sensor operation of an exemplary embodiment of the method and system of the present disclosure.

FIG. 10 illustrates a flow chart for the operation of the sensor of the method and system of the present disclosure. Specifically, when the sensor detects an event, such as new motion, change of state in motion, patient inclination, G-force, patient direction orientation, infrared beacon data received, etc., the sensor stores the sensed motion data with timestamp. The sensor then detects the motion event type, such as walking, sleeping, falling, sitting, shuffling, running, rolling, etc., and stores the sensed motion type data with timestamp. The sensor also detects the room/area where the motion event is occurring in and stores the room/area data with timestamp. The sensor next deduces the nature of the activity and stores the nature of activity data. If system communications are available, then the sensor sends the stored data, and any previously unsent stored data if available, to the system. If system communications are not available, the sensor clock timer is set, and subsequently triggers the sensor to check if communications are available to send unsent data.

Figure 11:
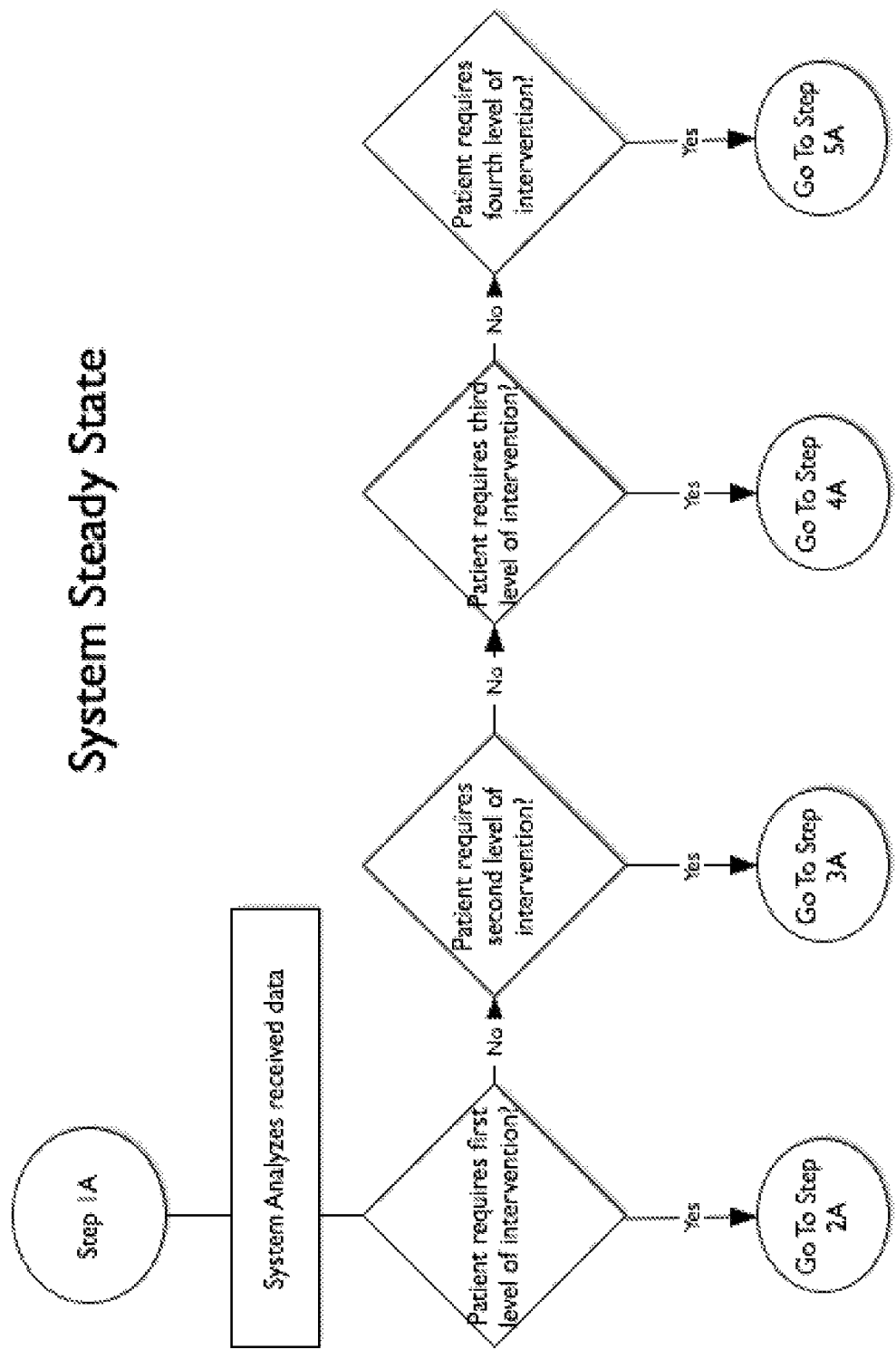
FIG. 11 is a flow chart for the system steady state of an exemplary embodiment of the method and system of the present disclosure.

FIG. 11-15 illustrate flow charts for the operation of the system of the method and system of the present disclosure. Specifically, FIG. 11 is a flow chart for the system steady nil state. When the system receives data, from the sensor (step 1A), the system analyzes the data that is received, and based upon the data received and the analysis thereof, determines what level of healthcare intervention is required. If the system determines that the patient requires a first level of intervention, then the system initiates the patient contact step 2A, illustrated in FIG. 12. If the system determines that the patient requires a second level of intervention, then the system initiates the resident caregiver contact step 3A, illustrated in FIG. 13. If the system determines that the patient requires a third level of intervention, then the system initiates the non-resident family member or friend contact step 4A, illustrated in FIG. 14. If the system determines that the patient requires a fourth level of intervention, then the system initiates the clinical contact step 5A, illustrated in FIG. 15.

Figure 12:
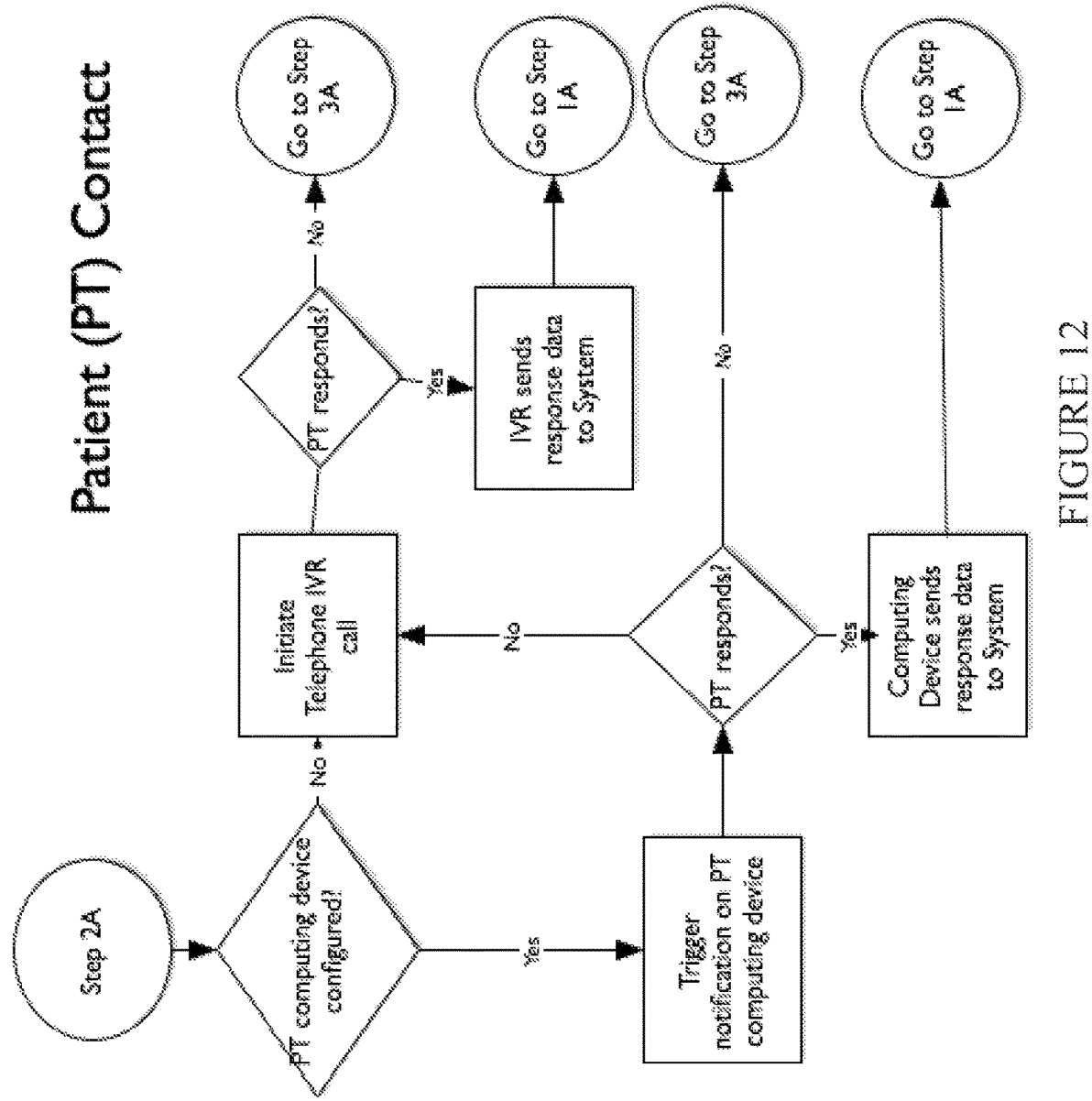
FIG. 12 is a flow chart for the patient contact intervention level of an exemplary embodiment of the method and system of the present disclosure.

FIG. 12 illustrates a flow chart for the patient contact intervention level (step 2A) of the method and system of the present disclosure. If a patient computing device is configured, then the system triggers notification on the patient computing device, discussed above with respect to FIG. 2. If the patient responds, then the patient computing device sends response data to the system, which proceeds back to step 1A. If the patient does not respond, then the system proceeds to step 3A. If a patient computing device is not configured, then the system initiates a telephone IVR call, discussed above with respect to FIG. 2. If the patient responds, then the IVR sends response data to the system, which proceeds back to step 1A. If the patient does not respond, then the system proceeds to step 3A.

Figure 13:
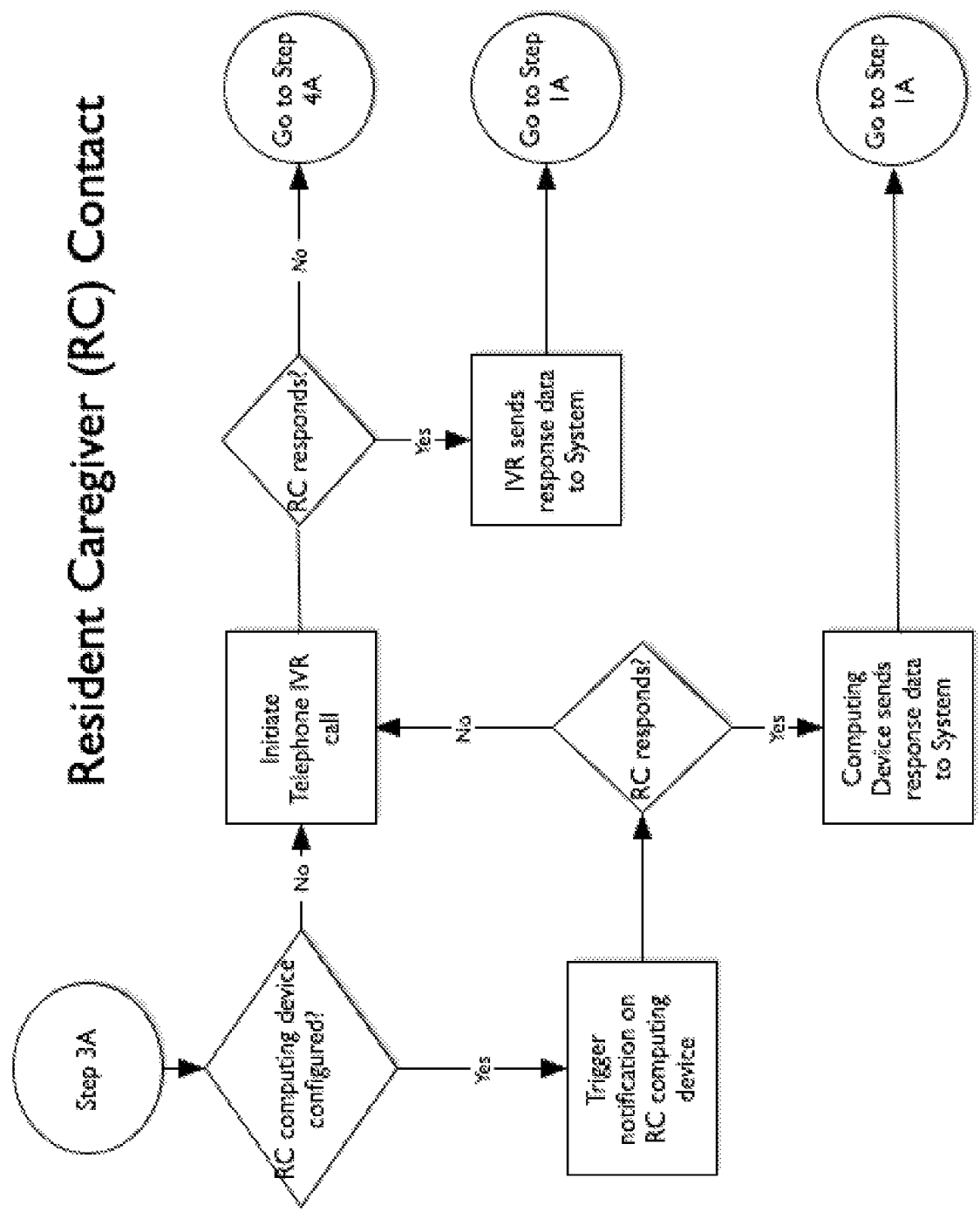
FIG. 13 is a flow chart for the resident caregiver contact intervention level of an exemplary embodiment of the method and system of the present disclosure.

FIG. 13 illustrates a flow chart for the resident caregiver contact intervention level (step 3A) of the method and system of the present disclosure. If a resident caregiver computing device is configured, then the system triggers notification on the resident caregiver computing device, discussed above with respect to FIG. 2. If the resident caregiver responds, then the resident caregiver computing device sends response data to the system, which proceeds back to step 1A. If the resident caregiver does not respond, then the system proceeds to step 4A. If a resident caregiver computing device is not configured, then the system initiates a telephone IVR call, discussed above with respect to FIG. 2. If the resident caregiver responds, then the IVR sends response data to the system, which proceeds back to step 1A. If the resident caregiver does not respond, then the system proceeds to step 4A.

Figure 14:
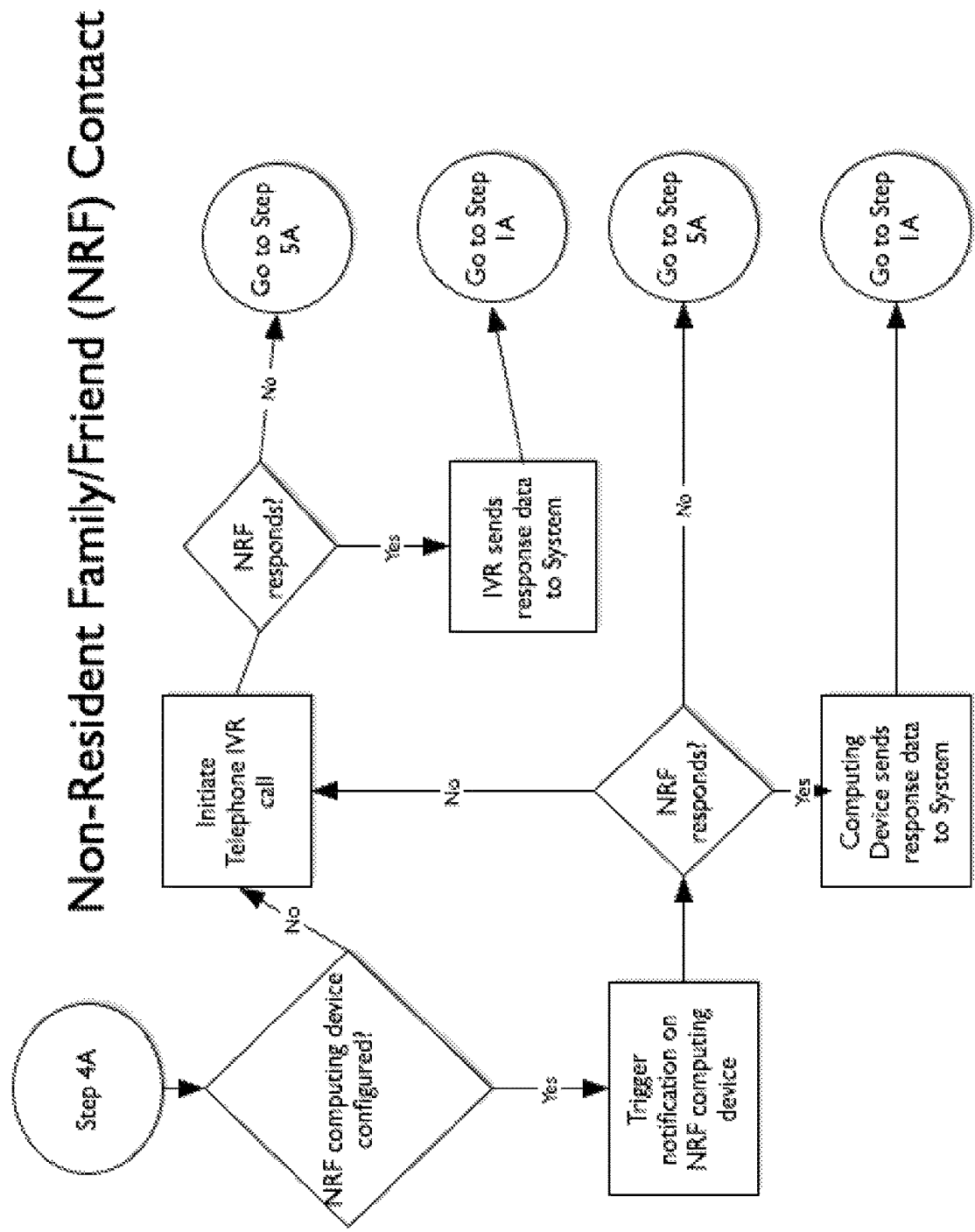
FIG. 14 is a flow chart for the non-resident caregiver contact intervention level of an exemplary embodiment of the method and system of the present disclosure.

FIG. 14 illustrates a flow chart for the non-resident family member or friend contact intervention level (step 4A) of the method and system of the present disclosure. If a non-resident family member or friend computing device is configured, then the system triggers notification on the non-resident family member or friend computing device, discussed above with respect to FIG. 2. If the non-resident family member or friend responds, then the non-resident family member or friend computing device sends response data to the system, which proceeds back to step 1A. If the non-resident family member or friend does not respond, then the system proceeds to step SA. If a non-resident family member or friend computing device is not configured, then the system initiates a telephone IVR call, discussed above with respect to FIG. 2. If the non-resident family member or friend responds, then the IVR sends response data to the system, which proceeds back to step 1A. If the non-resident family member or friend does not respond, then the system proceeds to step 5A.

Figure 15:
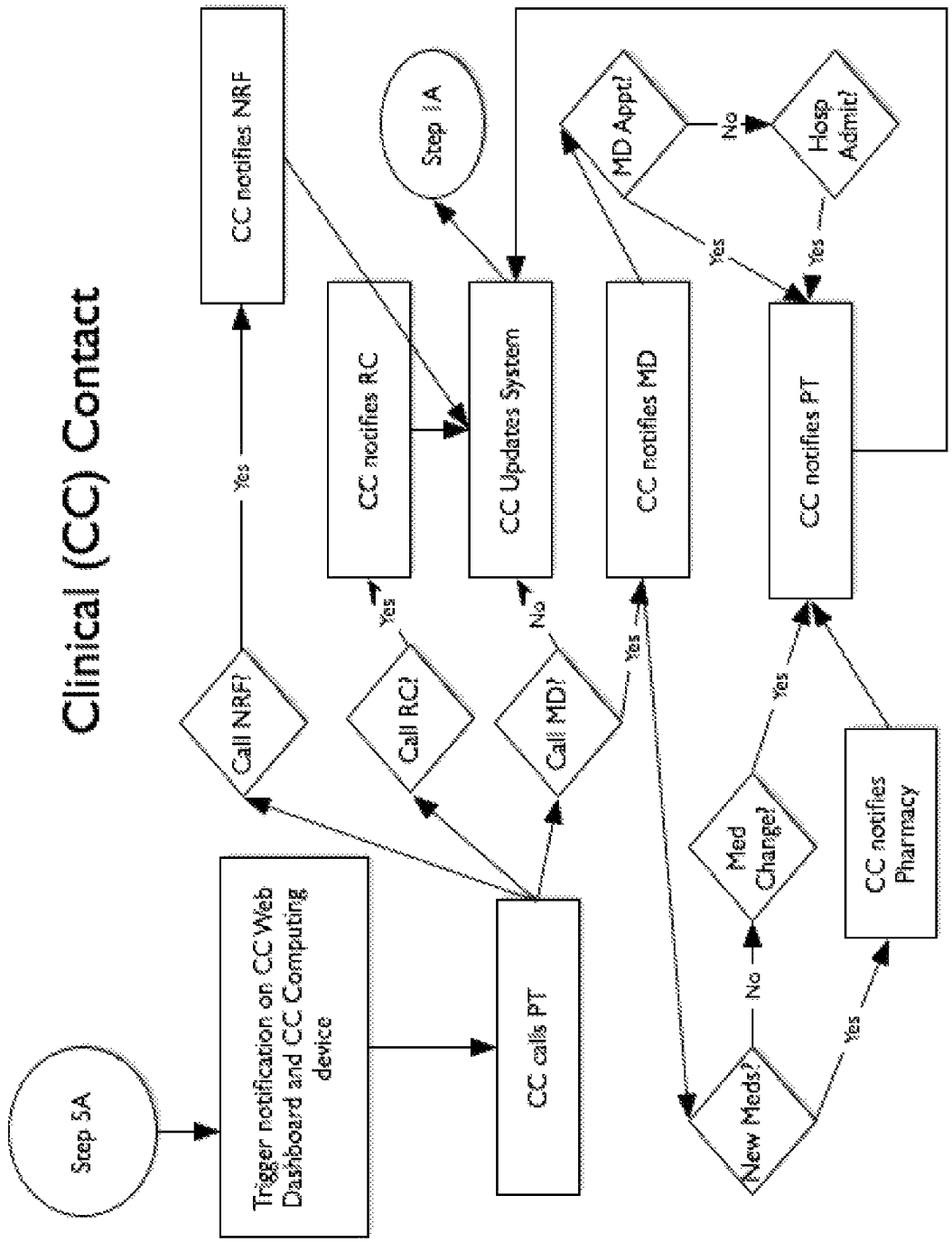
FIG. 15 is a flow chart for the clinical contact intervention level of an exemplary embodiment of the method and system of the present disclosure.

FIG. 15 illustrates a flow chart for the clinical contact intervention level (step 5A) of the method and system of the present disclosure. In this level of intervention, the system triggers notification on the clinical contact web dashboard or computing device. The clinical contact then can initiate calls to and or amongst the patient, the resident caregiver, the non-resident family member or friend, or the patient's doctor to obtain additional information, discussed above with respect to FIG. 2. Based upon the information gathered, the clinical contact can schedule a doctor visit, admit the patient to a hospital, communicate changes in medication or prescription of new medications and notify the pharmacy and the patient, etc. The clinical contact updates the system with all of the new data and information, and the system then proceeds back to step 1A.

Accordingly, from the above description, it can be seen that the disclosed methods and systems keep the patient in the lowest cost care setting, the home, and use a sentinel system utilising wearable sensors technology to determine when functional state is declining or patterns of activity change and trigger progressively higher levels of intervention, from "free" hands and eyes to skilled clinicians.

The Sensor and infrared beacon, or other room identifying devices, together allow for the detection of the room/area in which the patient activity is taking place. Thus, the Sensor detects not just the type of activity but where it is taking place so deductions can be made. For example, if the sensor detects a sitting posture and the room/area as Bathroom, the system can infer that the patient is using the toilet. If the sensor senses that the patient is standing and taking small steps, and room/area detected is the Kitchen, the system can infer that the patient is preparing food or drink. The sensor helps the system build a baseline of activity and also a "normal" pattern of daily behaviors for each patient.

The system can determine if the patient's functional state is declining. For example, the system can determine that a patient normally wakes up at 7:30 AM and walks on average 300 steps by 8 AM, but has now started walking far less in the same time. The system can also determine changes in a patient's pattern of activities. For example, the system can determine that a normal pattern of activity for a patient is to go from Bedroom to Bathroom, spend 20 minutes, go to Kitchen spend 10 minutes and then sit in the Living Room for the rest of the morning, but today the patient went from Bedroom to Bathroom and back to Bedroom where the patient stayed the whole morning in a prone position.

The system can determine additional data points on the progression of the disease state by presenting Observatory and Interrogatory questions to the Patient and others. The system can determine additional data points by prompting the patient to perform certain activities that are disease specific (for example: walk 10 steps) and then measuring the actual demonstrated activity and timing in real-time or near real-time via the sensor, as well as ask disease specific follow-up questions at the end of demonstration such as "are you short of breath" to further corroborate analysis.

When a pattern change or decline in functional activity is noticed, the system contacts the patient. The patient is contacted either via an App (if they are capable) or via Telephone IVR. The patient is asked questions that may encompass general, emotional state as well as disease specific. The questions are stored in the systems database(s) and are formed from established clinical guidelines (for example Seattle Obstructive Lung Disease Questionnaire, or SOLDQ in the case of a COPD patient), and responses are scored. The System can prompt the patient to perform a series of activities as part of the questionnaire and the Sensor can monitor and report back to the System in real-time or near real-time.

If a patient cannot be contacted or additional data points are needed, the system triggers the First Circle of Care: The Resident Caregiver (RC) if one is present (e.g., Spouse, Partner, Friend roommate) is contacted either via an App (if they are capable) or via Telephone IVR. The RC is presented with questions they can answer by Observing the patient. The RC is presented with questions that they can ask Patient (interrogatory component) and report answers back to the system. The questions asked are disease specific and based on established questionnaires in academic research.

If additional data points are needed, the system triggers the Second Circle of Care: The Non-Resident Family member or Friend (NRF) if one is present (e.g., Sibling, Adult Children, Friends) are contacted either via an App (if they are capable) or via Telephone IVR. The NRF is presented with questions they can answer by observing the patient. The NRF is presented with questions that they can ask Patient (interrogatory component) and report answers back to the system. The questions asked are disease specific and based on established questionnaires in academic research.

If analysis warrants further escalation, the system triggers the Third Circle of Care: The Clinical Contact (CC) at an ACO, MCO or LiveOps Center is contacted either via an App (if they are mobile) or via a web dashboard. The System displays patient history, its analysis thus far, questions and responses and scoring of answers from the Patient, RC and NRF as well as normal baseline functional scores and patterns of activity versus current observed anomalies for review. The CC reviews data and determines next course of action.

The CC uses human intelligence to determine the next appropriate course of action which maybe one or more of: Call Patient or RC or NRF to gather additional data; Dispatch a nurse/therapist for an onsite visit to verify clinical condition or perform a clinical intervention; Contact MD to review patient history and current state; Determine if change in medications or new medications are needed, and contact Pharmacy and Patient as needed; Schedule an office visit with MD if appropriate; and/or Schedule a hospital admission if appropriate. The CC then updates the System with all actions taken and any other relevant information.

Example of System in Use

The following narrative represents a hypothetical Use Case scenario illustrating the methods and systems of the present disclosure in use:

Mr. Jones is an 85 year old male patient in Florida. Mr. Jones lives at home with his spouse, 75 year old Mrs. Jones, who is of reasonable health. Mr. Jones is a Medicare beneficiary. The Jones have their son Sam, 48 years old, living 5 miles away and another son, Kyle, living in California. In addition, Mr. Jones close friend Mr. Pablo lives next door.

The Jones lives in a condo that has one bathroom, a living room, a bedroom, a kitchen and a dining room. The home has Internet access and Mrs. Jones is an avid user of a tablet computer. The Jones have a land line phone and a cell phone that Mrs. Jones carries. Sam and Kyle are avid users of smartphones and tablet computers. Mr. Pablo uses his desktop computer primarily to browse the Internet and to keep in touch with his family via email and social media.

Mr. Jones was diagnosed with a chronic care condition of Chronic Obstructive Pulmonary Disease (COPD) 5 years ago. Mr. Jones has been hospitalized for his condition several times. Mr. Jones uses a regimen of medication to manage his chronic disease, Mr. Jones was most recently discharged from the hospital a few days ago. At his discharge the Hospital and MD prescribed use of the disclosed system at no cost to Mr. Jones.

The hospital entered all of Mr. Jones information including his demographics, disease, etc., Mrs. Jones contact information, Sam and Kyle's information, as well as Mr. Pablo's information among others, into the system. A wearable sensor was fitted on Mr. Jones leg at his discharge and a self install kit of five Infrared (IR) beacons labeled "Kitchen", "Bathroom", Living Room", "Dining Room", "Bedroom" were provided to him, as well as a charger and a Base station with instructions on installation. Mr. Jones' son, Sam, came by to affix the small beacons in the respective rooms following the instructions on placement. The charging plate was installed by Mr. Jones' bed side, and Mr. Jones was instructed on removing the sensor and placing it on the charger plate for recharging when the sensor indicated that its battery was running low.

The base station was then plugged in and the Sensor was tapped three times to communicate with the base station and perform a communications system check. The Sensor is green LED lit to indicate success, and then Mr. Jones, following the installation instruction, walked into each of the separate rooms in turn. In each room, the sensor detected the distinct room by detecting the infrared beam and decoding the room ID contained in the beam for the specific room Mr. Jones was in, and vibrated and lit its green LED to indicate success.

The System sends Mrs. Jones a link to install Apps on her tablet computer, which she does successfully. The System sends Sam and Kyle a link to install Apps on their tablet computers and smartphones, which they successfully do. The System sends Mr. Pablo a link to install Apps on his desktop computer, which he does successfully.

Day 1-7: The sensor monitors Mr. Jones' activities over an initial period, for example seven days to create a baseline of normal activity and to note patterns of behavior. It determined on average that Mr. Jones woke up each day at 5:30 AM and walked about 250 steps in the 60 minutes. It noted that Mr. Jones went from the bedroom upon waking to the bathroom (taking about 30 seconds), where he spent 15 minutes and then he went to the kitchen where he spent 5 minutes and then went to the living room and sat for 2 hours. At about 8:00 AM, Mr. Jones went out of the condo (lack of IR signals, loss of connectivity to the base station) and walked for 30 minutes and then came back to the condo (detection of IR beams, regaining base station connectivity). Upon coming back in range the sensor transmitted the activity details that occurred when the sensor was out of range of the base station.

Day 7-14: The sensor continues to monitor Mr. Jones and no statistically significant variances in functional level or change in patterns of activity is detected by the system.

Day 15: The sensor detects normal pattern of activity but also that Jones is taking longer (but not statistically significant) to walk the same distances.

Day 16: The sensor detects variations in normal pattern of activity and that Mr. Jones is taking longer to walk the same distances (but neither is statistically significant). The system sends a push notification to Mrs. Jones and she responds on her app to several questions generated by the system from its databases based upon the sensed information:

a. Is Mr. Jones walking normally?—Yes
   b. Is he shuffling?—No
   c. Does he seem out of breath?—Yes
   d. Is he eating normally?—Yes The system records Mrs. Jones' responses for subsequent analysis.

Day 17: The sensor detects a normal pattern of activity, but also a statistically significant longer time to cover the same distances. The system calls Mr. Jones through its IVR telephone system and has him answer several questions:
   Are you feeling short of breath?
   b. Are you breathing heavily?
   c. Have you been practicing the energy conservation techniques taught at discharge?
   d. Do you have any pain?
   e. Are you feeling tired?

Based on Mr. Jones responses, the System sends a notification to Mrs. Jones and her App prompts her to answer some observational questions about Mr. Jones.
   a. Is Mr. Jones breathing laboriously?—Yes
   b. Was he snoring last night?—Yes
   c. Does he seem tired?—Yes
   d. Is his face puffy?—Yes
   e. Are his ankles swollen?—No The system records Mr. Jones' responses, and Mrs. Jones' responses for subsequent analysis.

Day 18: The sensor detects Mr. Jones waking up at 6:30 AM, goes to the bathroom for 10 minutes, then to the Kitchen and then Living room but returns to the bedroom where he lies down again for the next one hour. He has only taken 100 steps when normal activity is 250 steps. It also notes that the time taken to go from the bedroom to the bathroom is 60 seconds, statistically longer than the 30 second normal time. Sensor communicates this data to the System. The System determines an anomaly is occurring.

Since Mr. Jones does not use a computer, the System initiates an IVR Telephone call to the land line of the Jones residence, Mr. Jones picks up the phone and System identifies itself The System prompts Mr. Jones to "Press 1 if Mr. Jones is available to speak" or Press 2 for No. Mr. Jones presses 1. The System explains the reason for call: "we note that you did not follow your normal routines this morning." The System asks "Are you feeling unwell?" Press 1 for Yes, 2 for No. Mr. Jones responds with 1. The System then asks "Do you feel up to answering a few questions?" Press 1 for Yes, 2 for No. Mr. Jones responds with 2. The System then says, "Ok, please let Mrs. Jones know that we will contact her for some follow-up questions" and hangs up.

System next sends a push notification to Mrs. Jones tablet app. Mrs. Jones opens the App and the System notifies Mrs. Jones that: "We are contacting you as Mr. Jones seems unwell and we'd like to ask for your assistance in determining how he is feeling." The App requests Mrs. Jones to observe Mr. Jones and answer several observational questions:
   a. Is Mr. Jones ankles swollen?
   b. Is his skin color pale or normal?
   c. Does he have a fever?
   d. Is he coughing?
   e. Does he seem short of breath?
   f. Is he breathing heavily?
   g. Did he eat normally last night?
   h. Did he eat anything unusual last night?

After receiving responses to these questions, the App then asks Mrs. Jones to pose several interrogatory questions to Mr. Jones and enter his responses in the app. Specifically, in this scenario, the interrogatory questions are twenty questions from the Chronic Respiratory Disease Questionnaire (CRDQ) questionnaire to determine Dyspnea, Fatigue, Emotional burden and mastery of the disease, CRDQ is designed to be administered by an interviewer. All are multiple choice format and written for easy comprehension. Based on the entered responses, the system finds Mr. Jones' responses to the questions related to the emotional function to be outside the normal range.

The System then sends a push notification to Sam, Kyle and Mr. Pablo's computing devices, informing them of Mr. Jones' status, and optionally requesting that they take a desired action or respond to further questions. Sam decides that he will stop by on his way to work the next day to see how his dad is doing. Kyle is travelling and decides that when he gets home two days hence he will call Dad to see how he is doing. Mr. Pablo responds to the notification and walks over next door to Mr. Jones home to see how he is doing and "boost his spirits". He brings with him the newspaper to read stories to his friend and engage him. The Sensor detects in the meantime that Mr. Jones has visited the bathroom several more times during the day but is still going back to lie down. Mr. Jones has his dinner and goes to sleep.

Day 19: Mr. Jones wakes up the next day at 6:30 AM and walks to the bathroom, kitchen and then back to the bedroom. The System notes further decline in activity and larger change in pattern of normal behavior. The System triggers another notification to Mrs. Jones, Sam and Kyle. Sam stops by in the morning and the app on his smartphone prompts him to respond to a few observational questions:
   a. Is Mr. Jones ankles swollen?
   b. Is his skin color pale or normal?
   c. Does he have a fever?
   d. Is he coughing?
   e. Does he seem short of breath?
   f. Is he breathing heavily?
   g. How is his mood?

The App asks Sam to see if he can encourage his Dad to take a 6 minute walk test. Mr. Jones says Ok. Mr. Jones commences walking and the App on Sam's smartphone times him, while the sensor measures how many steps he has taken in the 6 minutes. However, Mr. Jones is unable to complete the test and stops after 1 minute. Sam is then prompted to ask Mr. Jones a follow-up question on if he is feeling short of breath and his response is entered. System determines that based on responses thus far, a nurse call is needed.

System initiates notification to the LiveOps center where a nurse gets a notification on her dashboard. The nurse reviews the information presented by System, for example, pattern change seen, and responses from Sam, Mrs. Jones and Mr. Pablo. The Nurse calls Mr. Jones to talk to him and to determine how he is feeling. The Nurse determines Mr. Jones is feeling short of breath and has trouble talking. The Nurse then calls the MD and discusses Mr. Jones' situation, and they decide a medication dose change is needed. The Nurse communicates the change in medication regimen to Mrs. Jones and Mr. Jones. As a result, Mr. Jones alters his medication.

The System continues to monitor his activity and patterns and sees improvements gradually. The System periodically pushes notifications to Mrs. Jones, Sam and Mr. Pablo to ask observational and interrogatory questions of Mr. Jones. System tracks that responses are trending positive. Over a period of a few days, Mr. Jones regains his normal pattern of activity.

The above scenario demonstrates the use of the system in a simple case where a slow functional decline is detected over a period of a few days. The use of spouse, family members and friends to conduct observational functions as well as interrogatory functions effectively removed the need for a nurse home visit in this case.

The use of the system as a sentinel effectively provided an early warning system that efficiently utilized higher levels of resources only when needed (Nurse/MD) to ultimately effect a medication change that made Mr. Jones feel better and prevented a continued decline in state of health that could have resulted in an ER visit or a hospital admission.

Without this system in place, it is conceivable that on Day 20 or Day 21 when decline is much greater, the Jones would have called their MD for advice, who then may simply schedule a nurse visit on Day 22 or perhaps an office appointment on Day 22 or simply, with an abundance of caution, direct Mr. Jones to the nearest ER. Alternately, by Day 22, by the time the nurse visits or the office visit is due, Mr. Jones health is significantly worse and he may end up going to ER in an ambulance anyway.

Since re-hospitalization was prevented, the hospital, which discharged Mr. Jones less than 30 days ago, does not have the financial burden of caring for Mr. Jones for free due to re-admission for the same diagnosis within 30 days after discharge. In addition, the ACO that the Hospital is part of now can show statistics that they have improved patient outcomes even when the patient is outside their care setting, by employing this remote monitoring sentinel system and thus be eligible for performance bonus from Medicare. Further, because the ACO and Hospital outcomes statistics are made public and ranked by Medicare, both entities stand to benefit by the better reputation for outcomes and quality and can attract more patients. In both cases the few hundred dollars the hospital or ACO spends on this sentinel system per month per patient saves them many thousands of dollars in potential revenue loss, gains of several thousands in performance dollars due to better outcomes and potentially a better reputation, which virtuously delivers more business.

The components of the system can take any suitable form, including any suitable hardware, software or other computerized components including but not limited to servers, processors, databases, memory devices, mobile applications, etc., capable of adequately performing their respective intended functions, as may be known in the art. Further, white the embodiment(s) are illustrative of the structure, function and operation of the exemplary method(s) and system(s), it should be understood that various modifications may be made thereto with departing from the teachings herein.

While the foregoing discussion presents the teachings in an exemplary fashion with respect to the disclosed methods and systems for remotely determining levels of healthcare interventions, it will be apparent to those skilled in the art that the present disclosure may apply to any type of method and system for monitoring a patient for healthcare purposes. Further, while the foregoing has described what are considered to be the best mode and/or other examples, it is understood that various modifications may be made therein and that the subject matter disclosed herein may be implemented in various forms and examples, and that the method(s) and system(s) may be applied in numerous applications, only some of which have been described herein.

What is claimed is:

1. A distributed and reconfigurable healthcare communication system comprising:
   a wearable sensor configured to continually monitor a wearer, the wearable sensor comprising:
      at least one sensing device configured to sense activity of the wearer and generate sensed activity data of the wearer, and
      a processor configured to identify a location of the wearer during the activity and determine a current functional activity of the wearer based on the sensed activity data and the identified location, the current functional activity and the corresponding identified location forming current state information; and
   at least one remote server, in communication with the wearable sensor via a communication network, configured to receive the current state information from the wearable sensor, and reconfigure the healthcare communication system by selectively incorporating one or more additional devices into said healthcare communication system under particular conditions to provide additional wearer data, by:
   detecting, by the at least one remote server, an event based on deviation of the current state information from at least one baseline activity pattern established for the wearer,
   for the detected event, determining, by the at least one remote server, a statistical significance of the deviation of the current state information relative to the at least one baseline activity pattern,
   for the statistical significance, determining, by the at least on remote server, a degree of the statistical significance, wherein the degree of the statistical significance corresponds to a degree of a care level to be selected,
   selecting, by the at least one remote server, a care level among a plurality of hierarchical care levels based on the statistical significance of the deviation, the degree of the statistical significance, and a previous health-state of the wearer, wherein the plurality of hierarchical care levels comprise at a lower care level corresponding to a lower degree statistical significance determined for the detected event and a higher care level corresponding to a higher degree of statistical significance determined for the detected event,
   transmitting, by the at least one remote server, a participation notification to a care level device associated with the selected care level, the participation notification based on at least one of the detected event, the selected care level and the previous health-state of the wearer, to incorporate the care level device into the healthcare communication system,
   causing, by the at least one remote server, the healthcare communication system to collect the additional wearer data via the incorporated device, and
   automatically, by the at least one remote server, updating the health-state of the wearer based on evaluation of the collected additional wearer data, the current state information, the detected event, and predetermined clinical guidelines, to determine whether to perform a further action by the remote server,
   wherein the further action includes obtaining additional health-state information of the wearer via a care level device of a different care level among the plurality of care levels, based on the updated health-state.

2. The system according to claim 1, further comprising:
   a plurality of beacons disposed in respective specific areas of a larger area, and configured to transmit a corresponding plurality of transmissions, each transmission including an identifier of the respective beacon associated with a corresponding area among the specific areas in which the respective beacon is disposed,
   wherein the wearable sensor is configured to receive at least one transmission among the plurality of transmissions, and
   the processor of the wearable sensor identifies the location of the wearer among the specific areas during the activity based on the corresponding identifier in the received at least one transmission.

3. The system of claim 2, wherein the sensed activity data includes motion of the wearer, the motion being inferred from changing beacon identifiers received by the wearable sensor.

4. The system of claim 2, wherein the plurality of beacons are infrared beacons.

5. The system of claim 1, wherein the at least one sensing device includes at least one of a gyro, an accelerometer, a magnetometer, an inclinometer, a thermometer, or a galvanic skin response sensor.

6. The system of claim 5, wherein the sensed activity data includes a direction of travel.

7. The system of claim 1, wherein the at least one sensing device includes an inclinometer and the sensed activity data includes a posture of the wearer.

8. The system of claim 1, wherein the baseline activity pattern corresponds to functional activity.

9. The system of claim 8, wherein the functional activity is at least one of walking, sitting, reclining, standing, and lying down.

10. The system of claim 1, further comprising means for receiving information from an external device, wherein the baseline activity pattern is established based at least in part on the received information.

11. The system of claim 1, wherein the collection of the additional wearer data, via the at least one remote server comprises establishing a communication session between the incorporated device and the at least one remote server, the remote server being configured to (i) transmit at least one event-specific request to the incorporated device and, (ii) receive sensor data generated by the wearable sensor during performance of the request.

12. The system of claim 1, wherein at least one of the actions and the further action is a disease-specific activity for a disease of the wearer.

13. The system of claim 1, further comprising a database, wherein the database stores, for the wearer, a list of contacts and one of the plurality of care levels associated with each of the contacts.

14. The system of claim 1, wherein the participation notification includes at least one of an observational component or an interrogatory component.

15. The system of claim 1, wherein the plurality of hierarchical care levels comprises at least three different care levels.

16. The system of claim 1, wherein the care level is selected from one of a patient care level, a caregiver care level and a clinical care level.

17. A distributed and reconfigurable healthcare communication system comprising:
a plurality of beacons disposed in respective specific areas of a larger area, and configured to transmit a corresponding plurality of transmissions, each transmission including an identifier of the respective beacon associated with a corresponding area among the specific areas in which the respective beacon is disposed;
a wearable sensor configured to receive at least one transmission among the plurality of transmissions and to continually monitor a wearer, the wearable sensor comprising:
at least one sensing device configured to sense activity of the wearer and generate sensed activity data of the wearer, and
a processor configured to: identify a location of the wearer among the specific areas during the activity based on the corresponding identifier in the received at least one transmission and determine a current functional activity of the wearer based on the sensed activity data and the identified location, the current functional activity and the corresponding identified location forming current state information; and
at least one remote server, in communication with the wearable sensor via a communication network, configured to receive the current state information from the wearable sensor, and reconfigure the healthcare communication system by selectively incorporating one or more additional devices into said healthcare communication system under particular conditions to provide additional wearer data, by:
detecting, by the at least one remote server, an event based on deviation of the current state information from at least one baseline activity pattern established for the wearer,
for the detected event, determining, by the at least one remote server, a statistical significance of the deviation of the current state information relative to the at least one baseline activity pattern,
for the statistical significance, determining, by the at least on remote server, a degree of the statistical significance, wherein the degree of the statistical significance corresponds to a degree of a care level to be selected,
selecting, by the at least one remote server, a care level among a plurality of hierarchical care levels based on the statistical significance of the deviation, the degree of the statistical significance, and a previous health-state of the wearer, wherein the plurality of hierarchical care levels comprise a lower care level corresponding to a lower degree statistical significance determined for the detected event and a higher care level corresponding to a higher degree of statistical significance determined for the detected event,
transmitting, by the at least one remote server, a participation notification to a care level device associated with the selected care level, the participation notification based on at least one of the detected event, the selected care level and the previous health-state of the wearer, to incorporate the care level device into the healthcare communication system,
causing, by the at least one remote server, the healthcare communication system to collect the additional wearer data via the incorporated device, and
automatically, by the at least one remote server, updating the health-state of the wearer based on evaluation of the collected additional wearer data, the current state information, the detected event, and predetermined clinical guidelines, to determine whether to perform a further action by the remote server,
wherein the further action includes obtaining additional health-state information of the wearer via a care level device of a different care level among the plurality of care levels, based on the updated health-state.

18. The system of claim 17, wherein the sensed activity data includes motion of the wearer, the motion being inferred from changing beacon identifiers received by the wearable sensor.

19. The system of claim 17, further comprising a database, wherein the database stores, for the wearer, a list of contacts and one of the plurality of care levels associated with each of the contacts.

20. The system of claim 17, wherein the participation notification includes at least one of an observational component or an interrogatory component.

21. The system of claim 17, wherein the plurality of hierarchical care levels comprises at least three different care levels.

22. A healthcare communication method for reconfiguring a distributed healthcare communication system, the method comprising the steps of:
sensing, by at least one sensing device of a wearable sensor of the healthcare communication system, activity of a wearer and generating sensed activity data of the wearer, the wearable sensor configured to continually monitor the wearer;
identifying, by a processor of the wearable sensor, a location of the wearer during the activity;
determining, by the processor of the wearable sensor, a current functional activity of the wearer based on the sensed activity data and the identified location, the current functional activity and the corresponding identified location forming current state information;
receiving, by at least one remote server of the healthcare communication system in communication with the wearable sensor via a communication network, the current state information from the wearable sensor; and
reconfiguring, by the at least one remote server, the healthcare communication system by selectively incorporating one or more additional devices into said healthcare communication system under particular conditions to provide additional wearer data, by:
detecting, by the at least one remote server, an event based on deviation of the current state information from at least one baseline activity pattern established for the wearer,
for the detected event, determining, by the at least one remote server, a statistical significance of the deviation of the current state information relative to the at least one baseline activity pattern, for the statistical significance, determining, by the at least on remote server, a degree of the statistical significance, wherein the degree of the statistical significance corresponds to a degree of a care level to be selected,
selecting, by the at least one remote server, a care level among a plurality of hierarchical care levels based on the statistical significance of the deviation, the degree of the statistical significance, and a previous health-state of the wearer, wherein the plurality of hierarchical care levels comprise a lower care level corresponding to a lower degree statistical significance determined for the detected event and a higher care level corresponding to a higher degree of statistical significance determined for the detected event,
selecting, by the at least one remote server, a care level among a plurality of hierarchical care levels based on the statistical significance of the deviation and a previous health-state of the wearer, at least one of a lower statistical significance or a lower health-state variation associated with a lower care level, and at least one of a higher statistical significance or a higher health-state variation associated with a higher care level,
transmitting, by the at least one remote server, a participation notification to a care level device associated with the selected care level, the participation notification based on at least one of the detected event, the selected care level and the previous health-state of the wearer, to incorporate the care level device into the healthcare communication system,
causing, by the at least one remote server, the healthcare communication system to collect the additional wearer data via the incorporated device, and
automatically, by the at least one remote server, updating the health-state of the wearer based on evaluation of the collected additional wearer data, the current state information, the detected event, and predetermined clinical guidelines, to determine whether to perform a further action by the remote server,
wherein the further action includes obtaining additional health-state information of the wearer via a care level device of a different care level among the plurality of care levels, based on the updated health-state.

23. The method of claim 22, further comprising the steps of:
transmitting a plurality of transmissions from a plurality of corresponding beacons of the healthcare system disposed in respective specific areas of a larger area, each transmission including an identifier of the respective beacon associated with a corresponding area among the specific areas in which the respective beacon is disposed
receiving, by the wearable sensor, at least one transmission among the plurality of transmissions; and
identifying, by the processor of the wearable sensor, the location of the wearer among the specific areas during the activity based on the corresponding identifier in the received at least one transmission.

24. The method of claim 23, wherein the sensed activity data includes motion of the wearer, the motion being inferred from changing beacon identifiers received by the wearable sensor.

25. The method of claim 22, wherein the stored at least one baseline activity pattern corresponds to functional activity.

26. The method of claim 25, wherein the functional activity is at least one of walking, sitting, reclining, standing, and lying down.

27. The method of claim 22, wherein the participation notification includes at least one of an observational component or an interrogatory component.

28. The method of claim 22, the collecting of the additional wearer data including the steps of: establishing a communication session between the incorporated device and the at least one remote server, transmitting at least one event-specific request to the incorporated device and receiving sensor data generated by the wearable sensor during performance of the request.

29. The method of claim 22, wherein the care level is selected from one of a patient care level, a caregiver care level and a clinical care level.

30. A distributed and reconfigurable healthcare communication system comprising:
at least one remote server, in communication with a wearable sensor via a communication network, configured to receive the current state information from the wearable sensor, the current state information comprising a sensed activity data, a location of the wearer during the sensed activity data, and a determined functional activity based on the sensed activity, and reconfigure the healthcare communication system by selectively incorporating one or more additional devices into said healthcare communication system under particular conditions to provide additional wearer data, by:
detecting, by the at least one remote server, an event based on deviation of the current state information from at least one baseline activity pattern established for the wearer,
for the detected event, determining, by the at least one remote server, a statistical significance of the deviation of the current state information relative to the at least one baseline activity pattern, for the statistical significance, determining, by the at least on remote server, a degree of the statistical significance, wherein the degree of the statistical significance corresponds to a degree of a care level to be selected, selecting, by the at least one remote server, a care level among a plurality of hierarchical care levels based on the statistical significance of the deviation, the degree of the statistical significance, and a previous health-state of the wearer, wherein the plurality of hierarchical care levels comprise a lower care level corresponding to a lower degree statistical significance determined for the detected event and a higher care level corresponding to a higher degree of statistical significance determined for the detected event, transmitting, by the at least one remote server, a participation notification to a care level device associated with the selected care level, the participation notification based on at least one of the detected event, the selected care level and the previous health-state of the wearer, to incorporate the care level device into the healthcare communication system, causing, by the at least one remote server, the healthcare communication system to collect the additional wearer data via the incorporated device, and automatically, by the at least one remote server, updating the health-state of the wearer based on evaluation of the collected additional wearer data, the current state information, the detected event, and predetermined clinical guidelines, to determine whether to perform a further action by the remote server, wherein the further action includes obtaining additional health-state information of the wearer via a care level device of a different care level among the plurality of care levels, based on the updated health-state.

* * * * *